United States Patent
Goodenow et al.

(10) Patent No.: US 10,226,472 B2
(45) Date of Patent: Mar. 12, 2019

(54) METHODS FOR THE TREATMENT OF BREAST CANCER

(75) Inventors: Robert Goodenow, San Clemente, CA (US); Peter Ordentlich, San Diego, CA (US)

(73) Assignee: SYNDAX PHARMACEUTICALS, INC., Waltham, MA (US)

( * ) Notice: Subject to any disclaimer, the term of this patent is extended or adjusted under 35 U.S.C. 154(b) by 0 days.

(21) Appl. No.: 14/342,354

(22) PCT Filed: Aug. 31, 2012

(86) PCT No.: PCT/US2012/053551
§ 371 (c)(1),
(2), (4) Date: May 20, 2014

(87) PCT Pub. No.: WO2013/033656
PCT Pub. Date: Mar. 7, 2013

(65) Prior Publication Data
US 2014/0378420 A1 Dec. 25, 2014

Related U.S. Application Data

(60) Provisional application No. 61/568,110, filed on Dec. 7, 2011, provisional application No. 61/628,999, filed on Nov. 12, 2011, provisional application No. 61/532,534, filed on Sep. 8, 2011, provisional application No. 61/530,873, filed on Sep. 2, 2011.

(51) Int. Cl.
| | |
|---|---|
| *A61K 31/566* | (2006.01) |
| *A61K 45/06* | (2006.01) |
| *A61K 31/4196* | (2006.01) |
| *A61K 31/4406* | (2006.01) |
| *A61K 31/5685* | (2006.01) |
| *G01N 33/483* | (2006.01) |
| *A61P 35/00* | (2006.01) |

(52) U.S. Cl.
CPC ........ *A61K 31/566* (2013.01); *A61K 31/4196* (2013.01); *A61K 31/4406* (2013.01); *A61K 31/5685* (2013.01); *A61K 45/06* (2013.01); *G01N 33/4833* (2013.01); *A61P 35/00* (2018.01); *G01N 2800/52* (2013.01)

(58) Field of Classification Search
None
See application file for complete search history.

(56) References Cited

U.S. PATENT DOCUMENTS

| | | | |
|---|---|---|---|
| 4,328,245 A | 5/1982 | Yu et al. | |
| 4,409,239 A | 10/1983 | Yu | |
| 4,410,545 A | 10/1983 | Yu et al. | |
| 6,350,458 B1 | 2/2002 | Modi | |
| 2009/0048156 A1 | 2/2009 | Brodie et al. | |
| 2010/0092992 A1 | 4/2010 | Hornbeck et al. | |
| 2010/0305167 A1 | 12/2010 | Burk et al. | |
| 2013/0004498 A1 | 1/2013 | Bai et al. | |

FOREIGN PATENT DOCUMENTS

| | | |
|---|---|---|
| WO | WO 2008/154382 A1 | 12/2008 |
| WO | WO 2012/151199 A1 | 11/2012 |
| WO | WO 2013/033656 A1 | 3/2013 |
| WO | WO 2013/163769 A1 | 11/2013 |

OTHER PUBLICATIONS

CN Patent Application No. 201280053368.3 Office Action dated Feb. 6, 2015.
EP Patent Application No. 12827961.8 European Search Report dated Dec. 5, 2014.
Korn et al, Clinical trial designs for cytostatic agents: Are new approaches needed? J Clin Oncol 19:265-272 (2001).
Linares et al., Manipulating protein acetylation in breast cancer: A promising approach in combination with hormonal therapies. Journal of Biomedicine and Biotechnology, 2011:1-15 (2010) Published online Dec. 6, 2010.
Lustberg et al., Epigenetic therapy in breast cancer. Curr. Breast Cancer Report, 3:34-43 (2011) Published online Dec. 22, 2010.
Rubinstein et al., Design issues of randomized Phase II trials and a proposal for Phase II screening trials. J Clin Oncol, 23:7199-7206 (2005).
Sabnis et al, Functional activation of the estrogen receptor-α and aromatase by the HDAC inhibitor entinostat sensitizes ER-negative tumors to letrozole. Cancer Res 71:1893-903 (2011).
Thompson and Siiteri, Utilization of oxygen and reduced nicotinamide adenine dinucleotide phosphate by human placental microsomes during aromatization of androstenedione. J. Biol. Chem., 249(17):5364-5372 (1974).
Tripathy et al, Phenotypic and proteomic alterations of acquired trastuzumab resistance. Journal of Clinical Oncology, 23(16S):3121 (2005) (Abstract only).
WO 2013/033656 IPRP issued Mar. 4, 2014.
WO 2013/033656 Written Opinion dated Feb. 1, 2013.
WO 2013/033656 ISR dated Feb. 1, 2013.
Wardley et al., Phase II data for entinostat, a class 1 selective histone deacetylase inhibitor, in patients whose breast cancer is progressing on aromatase inhibitor therapy. Journal of Clinical Oncology, American Society of Clinical Oncology, Mar. 20, 2010, p. 1052. (Abstract only).
Chinese Patent Application No. 201280053368.3 Second Office Action dated Sep. 17, 2015 (Full English translation provided).
Min Yan, et al., "Advances in aromatase inhibitors for breast cancer treatment." Foreign Medical Sciences (Cancer Section), vol. 30, No. 2, pp. 125-128, 2003. (No English language abstract was provided by the foreign associate).
Shaohua Zhang, et al., "A clinical study on the use of aromatase inhibitors in different order in the treatment of metastatic breast cancer." China Oncology, vol. 20, No. 5, pp. 385-359, 2010. (English language abstract provided).

(Continued)

*Primary Examiner* — Jean P Cornet
(74) *Attorney, Agent, or Firm* — Cooley LLP; Heidi A. Erlacher

(57) ABSTRACT

Described herein are methods for the treatment of breast cancer in a subject. In particular, methods are provided for the treatment of resistant, metastatic breast cancer with a combination of entinostat and an aromatase inhibitor.

18 Claims, 33 Drawing Sheets

(56) References Cited

OTHER PUBLICATIONS

Chung, E et al. "Assays for pharmacodynamic analysis of histone deacetylase inhibitors", *Expert Opinion Drug Metab Toxicol*, Apr. 2006, Pubmed Abstract PMID:16866608.
Lee, M.-J. et al. "Abstract B206: Pharmacokinetic and pharmacodynamic analysis of patients treated with the histone deacetylase inhibitor entinostat in combination with erlotinib", *Molecular Cancer Therapeutics*, 2009, vol. 8, Abstract No. B206 (1 page).
Masuda, N. et al. "A multicenter, randomized phase II study of neoadjuvant chemotherapy including trastuzumab with cyclophosphamide with docetaxel in patients with operable HER2-positive breast cancer (JBCRG-10 study)", *Journal of Clinical Oncology*, 2010, ASCO Annual Meeting Abstracts, vol. 28, No. 15 Suppl, 2010, Abstract No. 105, 2 pages.
Prince, H. et al. "Clinical Studies of Histone Deacetylase Inhibitors", *Clinical Cancer Research*, 2009, vol. 15, No. 12, p. 3958-3969.
San, S. et al. "Sequential Endocrine Therapy Based on Aromatase Inhibitor in Postmenopausal Women with Breast Cancer", *Clinical treatment of breast cancer* (in Japanese), 2010, vol. 25, No. 2, p. 235-242.
Bashuda H. et al. "Renal allograf rejection is prevented by adoptive transfer of anergic T cells in nonhuman primates", The Journal of Clinical Investigation, vol. 115, No. 7, p. 1896-1902 (2005).
Chung et al. "Histone Deacetylase Inhibitor Pharmacodynamic Analysis by Multiparameter Flow Cytometry", Annals of Clinical & Laboratory Science vol. 35, No. 4, p. 397-406, (2005).
Dincq S. et al. "Expression and Purification of Monospecific and Bispecific Recombinant Antibody Fragments Derived from Antibodies That Block the CD80/CD86-CD28 Costimulatory Pathway", Protein Expression and Purification, vol. 22, p. 11-24, (2001).
Kirk A. et al. "Induction Therapy with Monoclonal Antibodies Specific for CD80 and CD86 Delays the Onset of Acute renal Allograf Rejection in Non-human Primates", Transplantation, vol. 72, No. 3, p. 377-384 (2001).
Elsheikh, Somaia E. et al., "Global Histone Modifications in Breast Cancer Correlate with Tumor Phenotypes, Prognostic Factors, and Patient Outcome" Cancer Research 2009, vol. 69, No. 9, p. 3802-3809.
NCT00020579 from ClinicalTrials.gov dated Mar. 14, 2012, 14 pages.
NCT00101179 from ClinicalTrials.gov dated Jul. 16, 2018, 16 pages.
NCT00416130 from ClinicalTrials.gov dated Dec. 8, 2013, 7 pages.
NCT01132573 from ClinicalTrials.gov dated Jul. 16, 2014, 9 pages.
NCT01159418 from ClinicalTrials.gov dated Jul. 8, 2010, 9 pages.
NCT01234532 from ClinicalTrials.gov dated Oct. 2, 2017, 12 pages.
Ordentlich, P., "Abstract nr PR-6: Pharmacodynamic analysis of ENCORE 301, a placebo-controlled, randomized phase 2 study of exemestane with and without entinostat in postmenopausal ER+ breast cancer patients demonstrates an association of lysine hyperacetylation with clinical outcome" Molecular Cancer Therapeutics, 2011, vol. 10, Issue 11, 4 pages.
Sabnis, G.J et al., "Abstract PD05-03: HDAC Inhibitor Entinostat Restores Responsiveness of Letrozole Resistant MCF-7Ca Xenografts to AIs through Modulation of Her-2" Cancer Research, 2010, vol. 70, Issue 24, 4 pages.
Sabnis, G.J. et al., "HDAC Inhibitor Entinostat Restores Responsiveness of Letrozole-Reslstant MCF-7Ca Xenografts to Aromatase Inhibitors through Modulation of Her-2" Molecular Cancer Therapy, 2013, vol. 12, No. 12, p. 2804-2816.
Yardley, D.A. et al. "Results of ENCORE 301 a randomized, phase II, double-blind, placebo-controlled study of exemeStane with or without entinostat in postmenopausal women with locally recurrent or metastatic estrogen receptor-oosltive (ER+) breast cancer progressing on a nonsteroidal aromatase Inhibitor (AI)", presented Sep. 10, 2011, slides and presentation, 21 pages.

Key Inclusion Criteria and Stratifications

- Post-menopausal
- Confirmed ER+ breast cancer
- One prior chemotherapy in the metastatic setting allowed
- Relapsed on prior non-steroidal AI given as adjuvant after at least 12 months treatment

OR

- Progressed on prior non-steroidal AI in the advanced disease setting after at least 3 months treatment
- Stratified to ensure at least 80% patients had confirmed measurable disease (modeled on the EFECT study)

FIG. 2

Patients Mirror Those in Ph3 EFECT Study

| | | EFECT Study[1] Aromasin group n=342 | ENCORE-301[2] AROM/placebo n=63 | ENCORE-301[2] AROM/Entinostat n=64 |
|---|---|---|---|---|
| Age (yr) | Median | 63 | 62 | 63 |
| | <65 | 57% | 61% | 55% |
| | ≥65 | 43% | 39% | 45% |
| Sites of Metastases[3] | Bone | 66% | 71% | 77% |
| | Lung | 36% | 27% | 34% |
| | Liver | 32% | 45% | 27% |
| | Lymph nodes | 34% | 48% | 47% |
| | Visceral involvement | 58% | 67% | 53% |
| Sensitivity of disease[4] | AI-sensitive disease | 61% | 61% | 70% |
| | AI-resistant disease | 39% | 39% | 30% |
| Prior therapies | Last AI as adjuvant | 14% | 14% | 16% |
| | Last AI for advanced disease | 86% | 86% | 84% |
| | Chemo for advanced disease | 22% | 32% | 34% |
| WHO/ECOG Performance status | 0 (normal activity) | 53% | 76% | 63% |
| | 1 (restricted activity) | 44% | 24% | 38% |
| | 2 (in bed ≥ 50% of the time) | 4% | - | - |
| | Measurable disease | 79% | 82% | 81% |

[1] Chia et al, JCO 2008; [2] Full Analysis Set [3] Patients could have >1 site of metastases [4] Hormone sensitive defined as CR, PR or SD > 6 months during treatment with prior (last) AI for ABC. All other patients, including all those who received the AI as adjuvant therapy, defined as AI resistant

FIG. 4

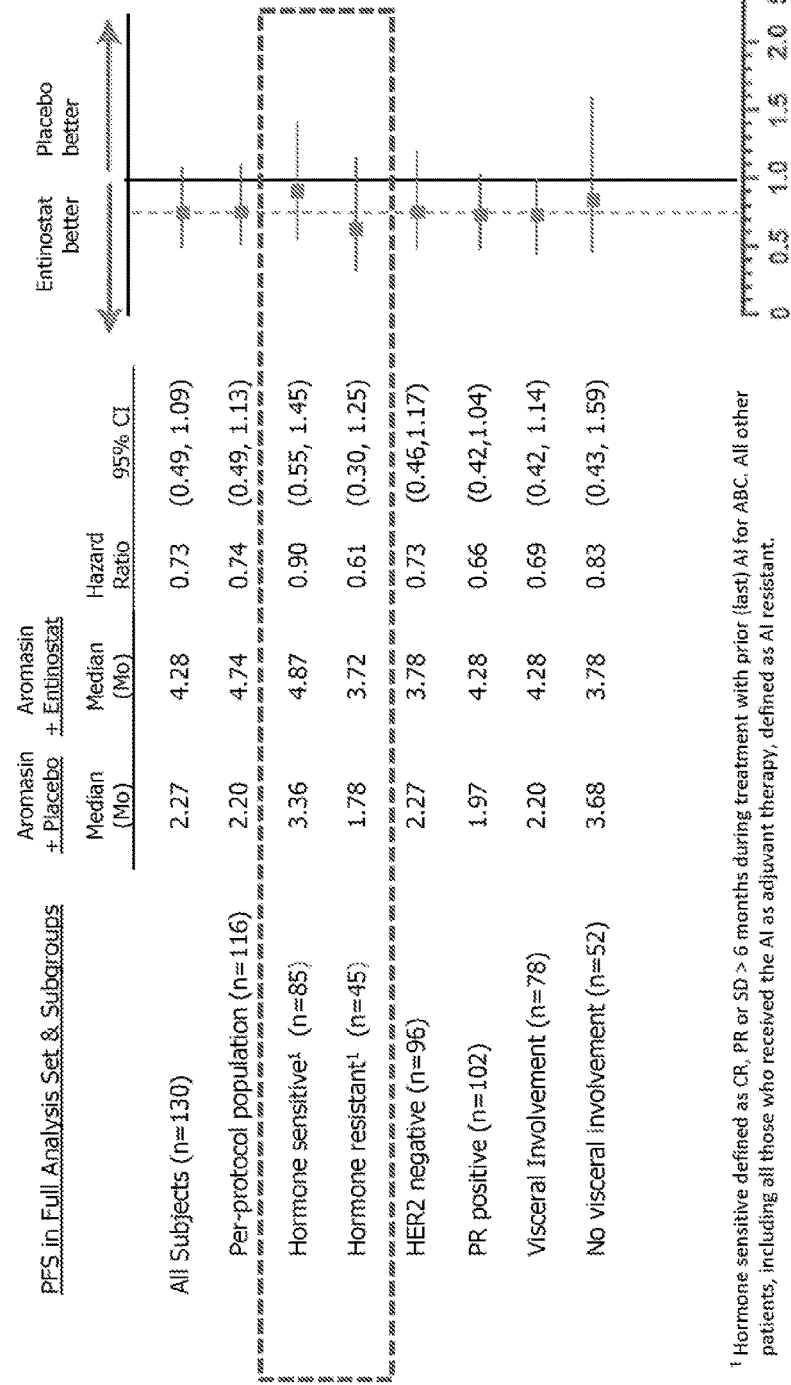

Hormone Resistant Patients May Benefit Most

| PFS in Full Analysis Set & Subgroups | Aromasin + Placebo Median (Mo) | Aromasin + Entinostat Median (Mo) | Hazard Ratio | 95% CI |
|---|---|---|---|---|
| All Subjects (n=130) | 2.27 | 4.28 | 0.73 | (0.49, 1.09) |
| Per-protocol population (n=116) | 2.20 | 4.74 | 0.74 | (0.49, 1.13) |
| Hormone sensitive[†] (n=85) | 3.36 | 4.87 | 0.90 | (0.55, 1.45) |
| Hormone resistant[†] (n=45) | 1.78 | 3.72 | 0.61 | (0.30, 1.25) |
| HER2 negative (n=96) | 2.27 | 3.78 | 0.73 | (0.46, 1.17) |
| PR positive (n=102) | 1.97 | 4.28 | 0.66 | (0.42, 1.04) |
| Visceral Involvement (n=78) | 2.20 | 4.28 | 0.69 | (0.42, 1.14) |
| No visceral involvement (n=52) | 3.68 | 3.78 | 0.83 | (0.43, 1.59) |

[†] Hormone sensitive defined as CR, PR or SD > 6 months during treatment with prior (last) AI for ABC. All other patients, including all those who received the AI as adjuvant therapy, defined as AI resistant.

FIG. 6

Most Frequent Adverse Events

Aromasin + Entinostat has acceptable safety profile

| Adverse Event | AROM+PLA (N=66) Any | G3 | G4 | AROM+ENT (N=63) Any | G3 | G4 |
|---|---|---|---|---|---|---|
| Fatigue | 17 (26%) | 2 3% | - | 29 (46%) | 7 11% | 1 2% |
| Nausea | 10 (15%) | 1 2% | - | 25 (40%) | 3 5% | - |
| Weight decreased | 12 (18%) | - | - | 11 (17%) | - | - |
| Anemia² | 8 (12%) | 1 2% | 1 2% | 12 (19%) | 1 2% | - |
| Back pain | 11 (17%) | 1 2% | - | 9 (14%) | - | - |
| Dyspnoea | 7 (11%) | - | - | 12 (19%) | 2 3% | - |
| Arthralgia | 11 (17%) | - | - | 7 (11%) | 1 2% | - |
| Diarrhoea | 8 (12%) | 1 2% | - | 10 (16%) | - | - |
| Constipation | 10 (15%) | 1 2% | - | 6 (10%) | - | - |
| Neutropenia¹,³ | 0 (0%) | - | - | 16 (25%) | 7 11% | 1 2% |
| Oedema peripheral | 3 (5%) | - | - | 13 (21%) | - | - |
| Vomiting | 3 (5%) | - | - | 13 (21%) | 3 5% | - |
| Thrombocytopenia³ | 4 (6%) | - | 1 2% | 11 (17%) | - | - |
| Pain | 4 (6%) | 1 2% | - | 10 (16%) | 1 2% | - |

¹ Occurring in >15% in either Group; Safety Population; Treatment-emergent Adverse Events, regardless of treatment-attribution.
² Composed of combined MedDRA preferred terms

FIG. 9

Summary

- Well conducted study
- Patient population mirrors EFECT
- Primary endpoint met
- Hormone resistance favored
- Early survival data encouraging
- Generally well tolerated

FIG. 10

PFS vs Protein Lysine Acetylation

Increased acetylation associated with improved PFS independent of treatment

CD19+ B-cells    CD14+ Monocytes    CD3+ T-cells

HR=0.556 (0.298, 1.037)    HR=0.609 (0.328, 1.132)    HR=0.750 (0.404, 1.390)

······· % Change ≤ Median
——— % Change > Median

FIG. 18

AEs vs PD Markers

| AE's with ≥10% difference between Treatments in Safety Population | AROM+ ENT | | | | | |
|---|---|---|---|---|---|---|
| | B-cells (%) | | T-cells (%) | | Monocytes (%) | |
| | Decrease N=14 | Increase N=13 | Decrease N=12 | Increase N=15 | Decrease N=12 | Increase N=15 |
| Fatigue | 11 (79%) | 9 (69%) | 9 (75%) | 11 (73%) | 9 (75%) | 11 (73%) |
| Nausea | 9 (64%) | 5 (38%) | 9 (64%) | 5 (38%) | 7 (58%) | 7 (47%) |
| Neutropenia group | 3 (21%) | 5 (38%) | 3 (25%) | 5 (33%) | 4 (33%) | 4 (27%) |
| Oedema peripheral | 3 (21%) | 4 (31%) | 3 (25%) | 4 (27%) | 3 (25%) | 4 (27%) |
| Vomiting | 3 (21%) | 2 (15%) | 1 (8%) | 4 (27%) | 0 | 5 (33%) |
| Thrombocytopenia group | 1 (7%) | 6 (46%) | 1 (8%) | 6 (40%) | 0 | 7 (47%) |
| Any of the above | 12 (86%) | 12 (92%) | 10 (83%) | 14 (93%) | 10 (83%) | 14 (93%) |

FIG. 21

AEs vs PD Markers – First 28 days

| AE's with ≥10% difference between Treatments in Safety Population | B-cells (%) | | T-cells (%) AROM+ ENT | | Monocytes (%) | |
|---|---|---|---|---|---|---|
| | Decrease N=14 | Increase N=13 | Decrease N=12 | Increase N=15 | Decrease N=12 | Increase N=15 |
| Fatigue | 8 (57%) | 6 (46%) | 6 (50%) | 8 (53%) | 7 (58%) | 7 (47%) |
| Nausea | 7 (50%) | 2 (15%) | 5 (42%) | 4 (27%) | 4 (33%) | 5 (33%) |
| Neutropenia group | 0 | 1 (8%) | 0 | 1 (7%) | 0 | 1 (7%) |
| Oedema peripheral | 1 (7%) | 1 (8%) | 1 (8%) | 1 (7%) | 1 (8%) | 1 (7%) |
| Vomiting | 3 (21%) | 1 (8%) | 1 (8%) | 3 (20%) | 0 | 4 (27%) |
| Thrombocytopenia group | 0 (7%) | 1 (8%) | 0 | 1 (7%) | 0 | 1 (7%) |
| Any of the above | 10 (71%) | 9 (69%) | 8 (67%) | 11 (73%) | 8 (67%) | 11 (73%) |

FIG. 22

Summary

- Largest treatment effect seen in the AROM + ENT hyper-acetylation group
  - Median PFS > 6 months
  - Although further follow-up required, OS trends consistent with PFS benefit
- Analysis of baseline characteristics revealed no evidence that differences between the AROM+ENT Increase and AROM+ENT Decrease groups were due to baseline imbalances between the two groups
- Data supports HDACi mechanism of action – increased protein lysine acetylation through inhibition of HDACs
- Early pharmacodynamic analysis of breast cancer patients receiving AROM + ENT may be used to select patients predicted to benefit the most

FIG. 23

Advancing Epigenetic Therapy in Breast Cancer

First positive, controlled study with epigenetic therapy in breast cancer

- Protein lysine acetylation linked to longer disease-free survival
- Hyperacetylation not associated with increased toxicity
- Findings may be linked to entinostat's differentiated pharmacology
- Data suggest that clinical gain can be determined after first or second dose of entinostat
- Validation of results planned in phase 3 study

FIG. 33

METHODS FOR THE TREATMENT OF BREAST CANCER

CROSS REFERENCE

This application is a US national phase application under 35 USC § 371 of international application PCT/US2012/053551, filed Aug. 31, 2012; which claims the benefit of U.S. Provisional Application No. 61/568,110, filed Dec. 7, 2011; U.S. Provisional Application No. 61/628,999, filed Nov. 12, 2011; U.S. Provisional Application No. 61/532,534, filed Sep. 8, 2011; and U.S. Provisional Application No. 61/530,873, filed Sep. 2, 2011, each of which is incorporated herein by reference in its entirety.

FIELD

The present invention relates to methods for the treatment of breast cancer based on the administration HDAC inhibitors and aromatase inhibitors.

BACKGROUND

Cancer, tumors, tumor-related disorders, and neoplastic disease states are serious and often times life-threatening conditions. These diseases and disorders, which are characterized by rapidly-proliferating cell growth, continue to be the subject of research efforts directed toward the identification of therapeutic agents which are effective in the treatment thereof. Such agents prolong the survival of the patient, inhibit the rapidly-proliferating cell growth associated with the neoplasm, or effect a regression of the neoplasm.

Generally, surgery and radiation therapy are the first modalities considered for the treatment of cancer that is considered locally confined, and offer the best prognosis. Chemotherapy treatment of certain cancers typically results in disappointing survival rates but still offer a survival benefit. For example, in patients with breast cancer, aromatase inhibitor chemotherapy regimens, such as the use of letrozole, anastrozole or exemestane, are employed. If patients fail to respond to an aromatase inhibitor treatment, additional conventional treatment offers limited benefit.

Despite the approval of several aromatase inhibitors for the treatment of early and late stage breast cancer, as with most therapeutic agents, side-effects result from its use. For example, common side effects include hot flashes, vasodilation and nausea. Of greater concern, is the growing view that, while utilization of aromatase inhibitors for the treatment of tumors may initially shrink the size of the tumor, the tumor may eventually enlarge in size, indicating, among other things, the development of resistance. Letrozole, a widely used aromatase inhibitor, may be representative of the types of therapeutic agents being used for cancer treatment; in that its use has an effect on cancer, but because of other factors, which are not entirely known, the tumor develops resistance and progresses.

HDAC inhibitors are an emerging class of therapeutic agents that promote differentiation and apoptosis in hematologic and solid malignancies through chromatin remodeling and gene expression regulation. Several HDAC inhibitors have been identified including benzamides (entinostat), short-chain fatty acids (i.e., Sodium phenylbutyrate); hydroxamic acids (i.e., suberoylanilide hydroxamic acid and thrichostatin A); cyclic tetrapeptides containing a 2-amino-8-oxo-9, 10-epoxy-decanoyl moiety (i.e., trapoxin A) and cyclic peptides without the 2-amino-8-oxo-9, 10-epoxy-decanoyl moiety (i.e., FK228). Entinostat (Syndax Pharmaceuticals, Inc.) is a benzamide HDAC inhibitor undergoing clinical investigation in multiple types of solid tumors and hematologic cancers. Entinostat is rapidly absorbed and has a half-life of about 100 hours; changes in histone acetylation have persisted for several weeks following the administration of entinostat.

What is needed, therefore, are compositions and/or methods of treatment for cancer which take advantage of the synergy found in a therapeutic combination that could increase the effectiveness of the agents and reduce and/or eliminate the side effects typically associated with conventional treatments.

SUMMARY OF THE INVENTION

One embodiment provides a method of treating breast cancer in a patient comprising (i) measuring the level of protein lysine acetylation prior to administration of entinostat-aromatase inhibitor combination therapy, (ii) administering entinostat-aromatase inhibitor combination therapy, (iii) measuring the level of protein lysine acetylation after administration of entinostat-aromatase inhibitor combination therapy, (iv) comparing the level of protein lysine acetylation after administration of entinostat-aromatase inhibitor combination therapy with the level of protein lysine acetylation prior to administration of entinostat-aromatase inhibitor combination therapy, and (v) continuing treatment with entinostat-aromatase inhibitor combination therapy if the level of protein lysine acetylation after administration of entinostat-aromatase inhibitor combination therapy is greater than the level of protein lysine acetylation prior to administration of entinostat-aromatase inhibitor combination therapy.

One embodiment provides a method of treating breast cancer in a patient comprising (i) administering entinostat-aromatase inhibitor combination therapy, and (ii) determining the change in protein lysine acetylation levels during the course of said therapy compared to pre-therapy protein lysine acetylation levels.

One embodiment provides a method of treating breast cancer in a patient comprising (i) determining the level prior to administration of protein lysine acetylation, (ii) administering entinostat-aromatase inhibitor combination therapy, and (iii) determining the level of protein lysine acetylation during the course of therapy.

Another embodiment provides the method wherein determining the change in protein lysine acetylation level during the course of said therapy occurs after about 2 days of therapy, about 5 days of therapy, about 7 days of therapy, about 15 days of therapy, or about 21 days of therapy.

Another embodiment provides the method wherein the protein lysine acetylation levels are obtained from a tissue sample selected from B-cells, T-cells, or monocytes.

Another embodiment provides the method wherein the aromatase inhibitor is exemestane. Another embodiment provides the method wherein the aromatase inhibitor is anastrozole. Another embodiment provides the method wherein the aromatase inhibitor is letrozole. Another embodiment provides the method wherein the aromatase inhibitor is administered daily. Another embodiment provides the method wherein the aromatase inhibitor is exemestane and is administered daily. Another embodiment provides the method wherein etinostat is administered every 7 days of a 28-day cycle. Another embodiment provides the method wherein the entinostat-aromatase inhibitor combination therapy comprises oral administration of entinostat every 7 days of a 28-day cycle, and oral administration of exemestane every day.

Another embodiment provides the method wherein the step of determining the protein lysine acetylation level during the course of therapy is performed more than once. Another embodiment provides the method wherein the step of determining the protein lysine acetylation level during the course of therapy is performed once.

Another embodiment provides the method further comprising selecting the patient for further treatment if the level of protein lysine acetylation level increases during the course of therapy.

Another embodiment provides the method further comprising selecting the patient for further treatment if the level of protein lysine acetylation level increases during the first week of the course of therapy. Another embodiment provides the method further comprising selecting the patient for further treatment if the level of protein lysine acetylation level increases during the first and second week of the course of therapy.

One embodiment provides a method of selecting a patient for further entinostat-aromatase inhibitor combination therapy comprising comparing the protein lysine acetylation level in a tissue sample obtained after initiating therapy to the protein lysine acetylation levels determined prior to initiating therapy.

One embodiment provides a method of selecting a patient for further entinostat-aromatase inhibitor combination therapy comprising comparing the protein lysine acetylation level in a tissue sample obtained after initiating therapy to the protein lysine acetylation levels determined prior to initiating therapy, wherein an increase in protein lysine acetylation level after initiating therapy indicates the patient will benefit from further therapy.

Another embodiment provides the method wherein the protein lysine acetylation level in a tissue sample obtained after initiating therapy is determined more than once. Another embodiment provides the method wherein increase in protein lysine acetylation level after initiating therapy occurs over a time period of one week. Another embodiment provides the method wherein the protein lysine acetylation level after initiating therapy is determined on days 2, 8 and 15.

Another embodiment provides the method wherein the increase is from about 10% to about 500%. Another embodiment provides the method wherein the increase is from about 10% to about 400%. Another embodiment provides the method wherein the increase is from about 10% to about 300%. Another embodiment provides the method wherein the increase is from about 10% to about 200%. Another embodiment provides the method wherein the increase is from about 10% to about 100%. Another embodiment provides the method wherein the increase is about 10%, about 20%, about 30%, about 40%, about 50% or about 60%. Another embodiment provides the method wherein the increase is about 25%, about 50%, about 75%, about 100%, about 125% or about 150%.

Another embodiment provides the method wherein the tissue sample is selected from B-cells, T-cells, or monocytes.

Another embodiment provides the method wherein the tissue sample obtained after initiating therapy is obtained at least 2 days after initiating therapy. Another embodiment provides the method wherein the tissue sample obtained after initiating therapy is obtained between day 2 and day 28 after initiating therapy. Another embodiment provides the method wherein the tissue sample obtained after initiating therapy is obtained on day 2, 3, 4, 5, 6, 7, 8, 9, 10, 11, 12, 13, 14 or 15 after initiating therapy.

One embodiment provides a method of selecting a patient for further entinostat-aromatase inhibitor combination therapy comprising comparing the percent change in protein lysine acetylation levels in a tissue sample obtained after initiating therapy to the protein lysine acetylation levels determined prior to initiating therapy, wherein a percent decrease in protein lysine acetylation levels after initiating therapy of about 5 percent to about 50 percent indicates the patient will not benefit from further therapy.

One embodiment provides a method of treating breast cancer which displays resistance to prior aromatase inhibitor therapy, the method comprising administering to a patient a combination comprising entinostat and an aromatase inhibitor, wherein the patient did not demonstrate a complete response, a partial response or stable disease for greater than six months during prior treatment with an aromatase inhibitor.

Another embodiment provides the method wherein the patient relapsed during treatment on or within 6 months of completion of prior non-steroidal aromatase inhibitor given as adjuvant therapy.

Another embodiment provides the method wherein the patient demonstrated progressive disease after at least 3 months treatment on prior non-steroidal aromatase inhibitor.

Another embodiment provides the method wherein the breast cancer is ER-positive.

Another embodiment provides the method wherein the aromatase inhibitor administered in combination with entinostat is letrozole. Another embodiment provides the method wherein the aromatase inhibitor administered in combination with entinostat is anastrozole. Another embodiment provides the method wherein the aromatase inhibitor administered in combination with entinostat is exemestane.

Another embodiment provides the method wherein entinostat and the aromatase inhibitor are administered sequentially in either order or simultaneously. Another embodiment provides the method wherein entinostat and the aromatase inhibitor are administered simultaneously. Another embodiment provides the method wherein the aromatase inhibitor is administered first. Another embodiment provides the method wherein the aromatase inhibitor is administered daily and the entinostat is administered periodically. Another embodiment provides the method wherein entinostat is administered weekly and the aromatase inhibitor is administered daily. Another embodiment provides the method wherein entinostat is introduced to an ongoing aromatase inhibitor course of therapy.

One embodiment provides a kit for treating aromatase inhibitor resistant breast cancer comprising a combination of entinostat and an aromatase inhibitor and instructions for the administration of the dosage form.

Another embodiment provides the kit, wherein the kit comprises one entinostat dosage form for every seven aromatase inhibitor dosage forms. Another embodiment provides the kit, wherein the kit comprises one entinostat dosage form for every 14 aromatase inhibitor dosage forms. Another embodiment provides the kit, wherein the kit comprises 4 entinostat dosage forms and 28 aromatase inhibitor dosage forms. Another embodiment provides the kit, wherein the kit comprises 4 entinostat dosage forms and 56 aromatase inhibitor dosage forms.

Another embodiment provides the kit wherein the aromatase inhibitor is letrozole. Another embodiment provides the kit wherein the aromatase inhibitor is anastrozole. Another embodiment provides the kit wherein the aromatase inhibitor is exemestane.

Another embodiment provides the method further comprising administering to the subject one or more therapies in addition to the combination of entinostat and the aromatase inhibitor selected from the group consisting of: letrozole, anastrozole or exemestane, or their pharmaceutically acceptable salts, solvates, or prodrugs.

Another embodiment provides the method wherein the one or more therapies comprise one or more of radiation therapy, chemotherapy, high dose chemotherapy with stem cell transplant, and monoclonal antibody therapy. Another embodiment provides the method wherein radiation therapy comprises internal and/or external radiation therapy. Another embodiment provides the method wherein the chemotherapy comprises administering to the subject one or more of doxorubicin, cyclophosphamide, paclitaxel, lapatinib, capecitabine, trastuzumab, bevacizumab, gemcitabine, eribulin, or nab-paclitaxel.

INCORPORATION BY REFERENCE

All publications, patents, and patent applications described in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2 provides a summary of inclusion criteria for the Phase 2 clinical trial;

FIG. 4 provides a detailed analysis of the patient population enrolled in the Phase 2 clinical trial;

FIG. 6 provides an analysis of benefit according to sub-group during the Phase 2 clinical trial;

FIG. 9 provides a summary of adverse events observed during in the Phase 2 clinical trial;

FIG. 10 provides a general summary of the Phase 2 clinical trial;

FIG. 18 provides a comparison of PFS to percent change of acetylation levels;

FIGS. 21 and 22 provide a summary of adverse events versus acetylation status;

FIG. 23 provides a summary of the interim biomarker study;

FIG. 33 provides a summary of the study which demonstrated that protein lysine acetylation is linked to longer disease-free survival.

DETAILED DESCRIPTION

Figure 1:
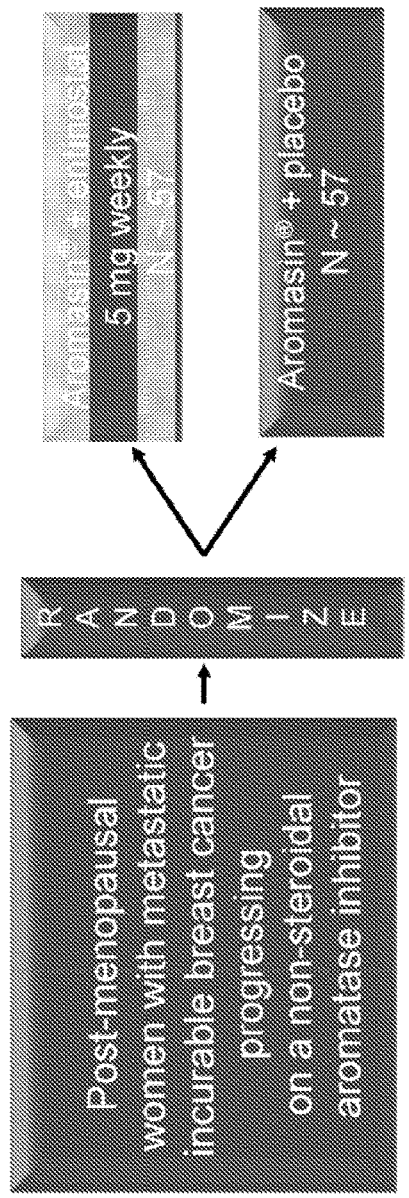
FIG. 1 provides a summary of the Phase 2 clinical trial.

Provided herein are methods of treating cancer based on the administration of an HDAC inhibitor and an aromatase inhibitor. The methods may further include treatments wherein the combination is supplemented with one or more therapeutic agents or therapies. The methods of treatment may incorporate patient selections based on levels of protein lysine acetylation observed during treatment.

To facilitate understanding of the disclosure set forth herein, a number of terms are defined below.

As used herein, "abnormal cell growth," refers to cell growth that is independent of normal regulatory mechanisms (e.g., loss of contact inhibition), including the abnormal growth of normal cells and the growth of abnormal cells.

"Neoplasia" as described herein, is an abnormal, unregulated and disorganized proliferation of cells that is distinguished from normal cells by autonomous growth and somatic mutations. As neoplastic cells grow and divide they pass on their genetic mutations and proliferative characteristics to progeny cells. A neoplasm, or tumor, is an accumulation of neoplastic cells. In some embodiments, the neoplasm can be benign or malignant.

"Metastasis," as used herein, refers to the dissemination of tumor cells via lymphatics or blood vessels. Metastasis also refers to the migration of tumor cells by direct extension through serous cavities, or subarachnoid or other spaces.

Through the process of metastasis, tumor cell migration to other areas of the body establishes neoplasms in areas away from the site of initial appearance.

As discussed herein, "angiogenesis" is prominent in tumor formation and metastasis. Angiogenic factors have been found associated with several solid tumors such as rhabdomyosarcomas, retinoblastoma, Ewing sarcoma, neuroblastoma, and osteosarcoma. A tumor cannot expand without a blood supply to provide nutrients and remove cellular wastes. Tumors in which angiogenesis is important include solid tumors such as renal cell carcinoma, hepatocellular carcinoma, and benign tumors such as acoustic neuroma, and neurofibroma. Angiogenesis has been associated with blood-born tumors such as leukemias. It is believed that angiogenesis plays a role in the abnormalities in the bone marrow that give rise to leukemia. Prevention of angiogenesis could halt the growth of cancerous tumors and the resultant damage to the subject due to the presence of the tumor.

The term "subject" refers to an animal, including, but not limited to, a primate (e.g., human), cow, sheep, goat, horse, dog, cat, rabbit, rat, or mouse. The terms "subject" and "patient" are used interchangeably herein in reference, for example, to a mammalian subject, such as a human subject.

The terms "treat," "treating," and "treatment" are meant to include alleviating or abrogating a disorder, disease, or condition; or one or more of the symptoms associated with the disorder, disease, or condition; or alleviating or eradicating the cause(s) of the disorder, disease, or condition itself.

The term "therapeutically effective amount" refers to the amount of a compound that, when administered, is sufficient to prevent development of, or alleviate to some extent, one or more of the symptoms of the disorder, disease, or condition being treated. The term "therapeutically effective amount" also refers to the amount of a compound that is sufficient to elicit the biological or medical response of a cell, tissue, system, animal, or human that is being sought by a researcher, veterinarian, medical doctor, or clinician.

The term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, excipient, solvent, or encapsulating material. Each component must be "pharmaceutically acceptable" in the sense of being compatible with the other ingredients of a pharmaceutical formulation. It must also be suitable for use in contact with the tissue or organ of humans and animals without excessive toxicity, irritation, allergic response, immunogenicity, or other problems or complications, commensurate with a reasonable benefit/risk ratio. See, *Remington: The Science and Practice of Pharmacy,* 21st Edition; Lippincott Williams & Wilkins: Philadelphia, Pa., 2005; *Handbook of Pharmaceutical Excipients,* 5th Edition; Rowe et al., Eds., The Pharmaceutical Press and the American Pharmaceutical Association: 2005; and *Handbook of Pharmaceutical Additives,* 3rd Edition; Ash and Ash Eds., Gower Publishing Company: 2007; *Pharmaceutical Preformulation and Formulation,* Gibson Ed., CRC Press LLC: Boca Raton, Fla., 2004).

The term "pharmaceutical composition" refers to a mixture of a compound disclosed herein with other chemical components, such as diluents or carriers. The pharmaceutical composition facilitates administration of the compound to an organism. Multiple techniques of administering a compound exist in the art including, but not limited to, oral, injection, aerosol, parenteral, and topical administration. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

Methods for the Treatment of Breast Cancer

One embodiment provides a method of treating breast cancer in a patient comprising (i) measuring the level of protein lysine acetylation prior to administration of entinostat-aromatase inhibitor combination therapy, (ii) administering entinostat-aromatase inhibitor combination therapy, (iii) measuring the level of protein lysine acetylation after administration of entinostat-aromatase inhibitor combination therapy, (iv) comparing the level of protein lysine acetylation after administration of entinostat-aromatase inhibitor combination therapy with the level of protein lysine acetylation prior to administration of entinostat-aromatase inhibitor combination therapy, and (v) continuing treatment with entinostat-aromatase inhibitor combination therapy if the level of protein lysine acetylation after administration of entinostat-aromatase inhibitor combination therapy is greater than the level of protein lysine acetylation prior to administration of entinostat-aromatase inhibitor combination therapy.

One embodiment provides a method of treating breast cancer in a patient comprising (i) administering entinostat-aromatase inhibitor combination therapy, and (ii) determining the change in protein lysine acetylation levels during the course of said therapy compared to pre-therapy protein lysine acetylation levels.

One embodiment provides a method of treating breast cancer in a patient comprising (i) determining the level prior to administration of protein lysine acetylation, (ii) administering entinostat-aromatase inhibitor combination therapy, and (iii) determining the level of protein lysine acetylation during the course of therapy.

Another embodiment provides the method wherein determining the change in protein lysine acetylation level during the course of said therapy occurs after about 2 days of therapy, about 5 days of therapy, about 7 days of therapy, about 15 days of therapy, or about 21 days of therapy.

Another embodiment provides the method wherein the protein lysine acetylation levels are obtained from a tissue sample selected from B-cells, T-cells, or monocytes.

Another embodiment provides the method wherein the aromatase inhibitor is exemestane. Another embodiment provides the method wherein the aromatase inhibitor is anastrozole. Another embodiment provides the method wherein the aromatase inhibitor is letrozole. Another embodiment provides the method wherein the aromatase inhibitor is administered daily. Another embodiment provides the method wherein the aromatase inhibitor is exemestane and is administered daily. Another embodiment provides the method wherein etinostat is administered every 7 days of a 28-day cycle. Another embodiment provides the method wherein the entinostat-aromatase inhibitor combination therapy comprises oral administration of entinostat every 7 days of a 28-day cycle, and oral administration of exemestane every day.

Another embodiment provides the method wherein the step of determining the protein lysine acetylation level during the course of therapy is performed more than once. Another embodiment provides the method wherein the step of determining the protein lysine acetylation level during the course of therapy is performed once.

Another embodiment provides the method further comprising selecting the patient for further treatment if the level of protein lysine acetylation level increases during the course of therapy.

Another embodiment provides the method further comprising selecting the patient for further treatment if the level of protein lysine acetylation level increases during the first week of the course of therapy. Another embodiment provides the method further comprising selecting the patient for further treatment if the level of protein lysine acetylation level increases during the first and second week of the course of therapy.

One embodiment provides a method of selecting a patient for further entinostat-aromatase inhibitor combination therapy comprising comparing the protein lysine acetylation level in a tissue sample obtained after initiating therapy to the protein lysine acetylation levels determined prior to initiating therapy.

One embodiment provides a method of selecting a patient for further entinostat-aromatase inhibitor combination therapy comprising comparing the protein lysine acetylation level in a tissue sample obtained after initiating therapy to the protein lysine acetylation levels determined prior to initiating therapy, wherein an increase in protein lysine acetylation level after initiating therapy indicates the patient will benefit from further therapy.

Another embodiment provides the method wherein the protein lysine acetylation level in a tissue sample obtained after initiating therapy is determined more than once. Another embodiment provides the method wherein increase in protein lysine acetylation level after initiating therapy occurs over a time period of one week. Another embodiment provides the method wherein the protein lysine acetylation level after initiating therapy is determined on days 2, 8 and 15.

Another embodiment provides the method wherein the increase is from about 10% to about 500%. Another embodiment provides the method wherein the increase is from about 10% to about 400%. Another embodiment provides the method wherein the increase is from about 10% to about 300%. Another embodiment provides the method wherein the increase is from about 10% to about 200%. Another embodiment provides the method wherein the increase is from about 10% to about 100%. Another embodiment provides the method wherein the increase is about 10%, about 20%, about 30%, about 40%, about 50% or about 60%. Another embodiment provides the method wherein the increase is about 25%, about 50%, about 75%, about 100%, about 125% or about 150%.

Another embodiment provides the method wherein the tissue sample is selected from B-cells, T-cells, or monocytes.

Another embodiment provides the method wherein the tissue sample obtained after initiating therapy is obtained at least 2 days after initiating therapy. Another embodiment provides the method wherein the tissue sample obtained after initiating therapy is obtained between day 2 and day 28 after initiating therapy. Another embodiment provides the method wherein the tissue sample obtained after initiating therapy is obtained on day 2, 3, 4, 5, 6, 7, 8, 9, 10, 11, 12, 13, 14 or 15 after initiating therapy.

One embodiment provides a method of selecting a patient for further entinostat-aromatase inhibitor combination therapy comprising comparing the percent change in protein lysine acetylation levels in a tissue sample obtained after initiating therapy to the protein lysine acetylation levels determined prior to initiating therapy, wherein a percent decrease in protein lysine acetylation levels after initiating therapy of about 5 percent to about 50 percent indicates the patient will not benefit from further therapy.

One embodiment provides a method of treating breast cancer which displays resistance to prior aromatase inhibitor therapy, the method comprising administering to a patient a combination comprising entinostat and an aromatase inhibitor, wherein the patient did not demonstrate a complete response, a partial response or stable disease for greater than six months during prior treatment with an aromatase inhibitor.

Another embodiment provides the method wherein the patient relapsed during treatment on or within 6 months of completion of prior non-steroidal aromatase inhibitor given as adjuvant therapy.

Another embodiment provides the method wherein the patient demonstrated progressive disease after at least 3 months treatment on prior non-steroidal aromatase inhibitor.

Another embodiment provides the method wherein the breast cancer is ER-positive.

Another embodiment provides the method wherein the aromatase inhibitor administered in combination with entinostat is letrozole. Another embodiment provides the method wherein the aromatase inhibitor administered in combination with entinostat is anastrozole. Another embodiment provides the method wherein the aromatase inhibitor administered in combination with entinostat is exemestane.

Another embodiment provides the method wherein entinostat and the aromatase inhibitor are administered sequentially in either order or simultaneously. Another embodiment provides the method wherein entinostat and the aromatase inhibitor are administered simultaneously. Another embodiment provides the method wherein the aromatase inhibitor is administered first. Another embodiment provides the method wherein the aromatase inhibitor is administered daily and the entinostat is administered periodically. Another embodiment provides the method wherein entinostat is administered weekly and the aromatase inhibitor is administered daily. Another embodiment provides the method wherein entinostat is introduced to an ongoing aromatase inhibitor course of therapy.

One embodiment provides a kit for treating aromatase inhibitor resistant breast cancer comprising a combination of entinostat and an aromatase inhibitor and instructions for the administration of the dosage form.

Another embodiment provides the kit, wherein the kit comprises one entinostat dosage form for every seven aromatase inhibitor dosage forms. Another embodiment provides the kit, wherein the kit comprises one entinostat dosage form for every 14 aromatase inhibitor dosage forms. Another embodiment provides the kit, wherein the kit comprises 4 entinostat dosage forms and 28 aromatase inhibitor dosage forms. Another embodiment provides the kit, wherein the kit comprises 4 entinostat dosage forms and 56 aromatase inhibitor dosage forms.

Another embodiment provides the kit wherein the aromatase inhibitor is letrozole. Another embodiment provides the kit wherein the aromatase inhibitor is anastrozole. Another embodiment provides the kit wherein the aromatase inhibitor is exemestane.

Another embodiment provides the method further comprising administering to the subject one or more therapies in addition to the combination of entinostat and the aromatase inhibitor selected from the group consisting of: letrozole, anastrozole or exemestane, or their pharmaceutically acceptable salts, solvates, or prodrugs.

Another embodiment provides the method wherein the one or more therapies comprise one or more of radiation therapy, chemotherapy, high dose chemotherapy with stem cell transplant, and monoclonal antibody therapy. Another embodiment provides the method wherein radiation therapy comprises internal and/or external radiation therapy. Another embodiment provides the method wherein the chemotherapy comprises administering to the subject one or more of doxorubicin, cyclophosphamide, paclitaxel, lapatinib, capecitabine, trastuzumab, bevacizumab, gemcitabine, eribulin, or nab-paclitaxel.

Histone Deacetylase

The HDACs are a family including at least eighteen enzymes, grouped in three classes (Class I, II and III). Class I HDACs include, but are not limited to, HDACs 1, 2, 3, and 8. Class I HDACs can be found in the nucleus and are believed to be involved with transcriptional control repressors. Class II HDACs include, but are not limited to, HDACS 4, 5, 6, 7, and 9 and can be found in both the cytoplasm as well as the nucleus. Class III HDACs are believed to be NAD dependent proteins and include, but are not limited to, members of the Sirtuin family of proteins. Non-limiting examples of sirtuin proteins include SIRT1-7. As used herein, the term "selective HDAC" refers to an HDAC inhibitor that does not interact with all three HDAC classes.

HDAC Inhibitors

HDAC inhibitors can be classified broadly into pan HDAC inhibitors and selective HDAC inhibitors. Although there is a large structural diversity of known HDAC inhibitors, they share common features: a part that interacts with the enzyme active site and a side-chain that sits inside the channel leading to the active site. This can be seen with the hydroxamates such as SAHA, where the hydroxamate group is believed to interact with the active site. In the case of the depsipeptides, it is believed that an intracellular reduction of the disulphide bond creates a free thiol group (which interacts with the active site) attached to a 4-carbon alkenyl chain. A difference between the HDAC inhibitors is in the way that they interact with the rim of the HDAC channel, which is at the opposite end of the channel to the active site. It is this interaction, between the HDAC inhibitor and the rim of the channel, which is believed to account, at least in part, for some observed differences in HDAC selectivity between pan-HDAC inhibitors, such as SAHA and selective HDAC inhibitors such as the depsipeptides. A particularly preferred HDAC inhibitor is entinostat. Entinostat has the chemical name N-(2-aminophenyl)-4-[N-(pyridine-3-yl) methoxycarbonylamino-methyl]-benzamide and the chemical structure shown below.

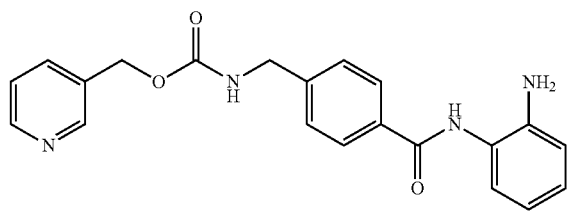

Chemical structure of entinostat

Aromatase

Estrogen is one of the female sex hormones and has many functions in the body. It has been found that about 80% of breast cancer tumors overexpress the estrogen receptor and respond positively to the presence of estrogen. In postmenopausal women, ovarian estrogen production is reduced and plasma estrogen levels are generally lower than in premenopausal women.

A residual source of estrogen in post-menopausal women is the synthesis of estrogens from androgens, which is catalyzed by aromatase. Inhibition of aromatase activity should lead to a reduction in the levels of estrogen and therefore a reduction in the growth of breast cancer tumors which respond positively to the presence of estrogen.

Aromatase is an enzyme of the cytochrome P450 family and a product of the CYP19 gene. The chemical function of aromatase is to convert testosterone to estradiol and androstenedione to estrone.

Aromatase Inhibitors

Aromatase inhibitors decrease the body's estrogen by blocking the enzyme aromatase from turning androgen into estrogen. For the treatment of early stage breast cancer, certain aromatase inhibitors may be used as adjuvant therapy instead of tamoxifen or after 2 or more years of tamoxifen. For the treatment of metastatic breast cancer, aromatase inhibitors are being tested in clinical trials to compare them to hormone therapy with tamoxifen.

As described herein, an "aromatase inhibitor" is a molecule which inhibits the activity of the aromatase enzyme. Compounds which are inhibitors of aromatase can be readily identified by one skilled in the art using methods such as, for example, standard pharmacological test procedures which measure the inhibition of the conversion of 1,2-$^3$H-androstenedione to estrone.

In brief, a microsomal fraction is prepared from human placenta by the method as described by Thompson and Siiteri (J. Biol. Chem., Vol. 249, p. 5364 (1974)). The microsomal preparation so obtained is lyophilized and stored at −40° C. The human placental microsomes are added to 1,2-$^3$H-androstenedione and incubated for 20 minutes at 37° C. The amount of aromatization of the labelled substrate is detected by the loss of $^3$H$_2$O into the incubation medium. The substrate is removed by chloroform extraction, followed by adsorption to charcoal in suspension. The charcoal is removed by centrifugation and the steroid-free medium is counted in a liquid scintillation counter. Compositions are tested for aromatase inhibitory activity by adding them to the incubation medium prior to the addition of the microsomes. The relative cpm obtained with and without the composition is used to calculate the percent inhibition of the aromatization of androstenedione to estrone. IC$_{50}$ values can be determined graphically as the concentration of test composition at which the aromatization of androstenedione to estrone is reduced to 50% of control value.

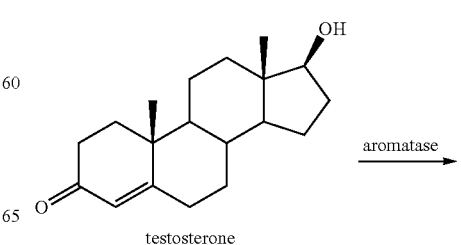

testosterone

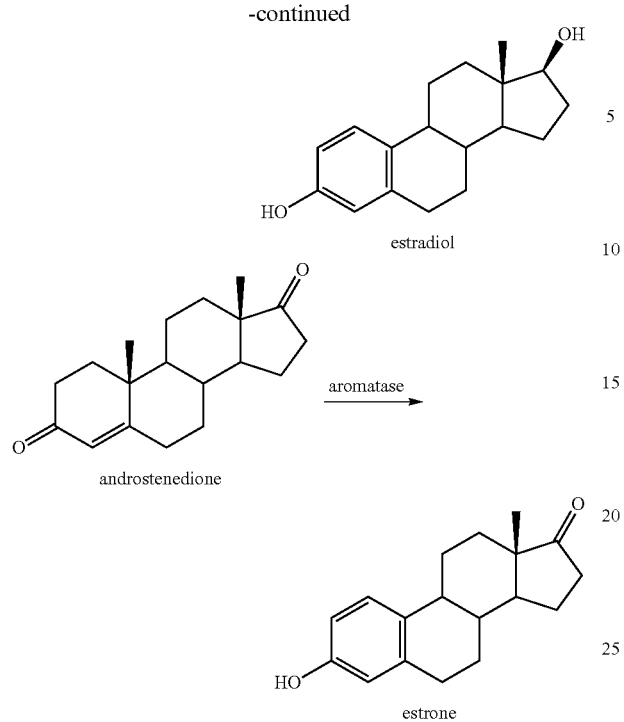

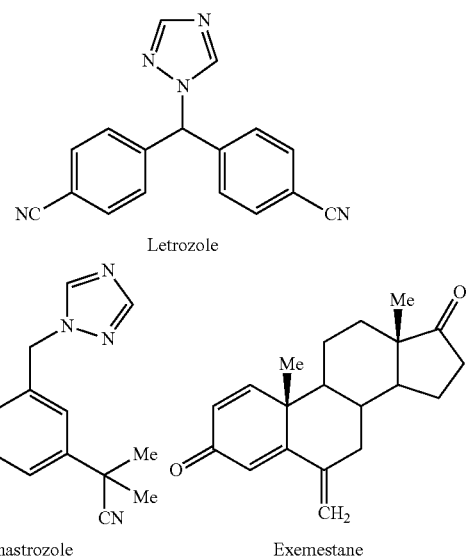

Subcutaneous fat is a major site of aromatase activity and it has been suggested that plasma estrogen levels correlate with body-mass index (Longcope et al, Metabolism 1986, 35, 235-7). It has been suggested that at menopause, plasma estrogen levels fall from about 110 pg/mL to a much lower level of about 7 pg/mL. However, in post-menopausal women, the intra-tumoral concentration of estradiol has been found to be about 10 times higher than in the plasma, probably due to aromatase activity within the tumor.

Inhibition of aromatase as a treatment option for breast cancer has been studied with some success. Currently three aromatase inhibitors are approved for marketing in the US for the treatment of breast cancer, at various stages, in post-menopausal women. Letrozole (Femara®) is indicated for several treatment options including, extended adjuvant treatment of early breast cancer in postmenopausal women with 5 years prior tamoxifen treatment, treatment of post menopausal women with hormone receptor positive (or unknown) locally advanced or metastatic breast cancer and advanced breast cancer treatment in postmenopausal women with disease progression following antiestrogen therapy.

Anastrozole (Arimidex®) is indicated for several treatment options including, adjuvant treatment of postmenopausal women with hormone receptor-(+) early breast cancer, first-line treatment of post menopausal women with hormone receptor-(+) (or unknown) locally advanced or metastatic breast cancer and advanced breast cancer in postmenopausal women with disease progression following tamoxifen therapy.

Exemestane (Aromasin®) is indicated for several treatment options including, adjuvant treatment of postmenopausal women with estrogen-receptor-(+) early breast cancer who have received 2-3 years of tamoxifen treatment and advanced breast cancer in postmenopausal women with disease progression following tamoxifen therapy.

These drugs are grouped into two classes: (Type 1) exemestane is based on a steroid chemical structure and (type 2) letrozole and anastrozole are based on a non-steroidal chemical structure. Clinical trials have shown letrozole to be superior to tamoxifen in the treatment of advanced ER(+) disease. In early disease, adjuvant therapy with anastrozole appears to be superior to therapy with tamoxifen in reducing risk of relapse. Recent clinical trial results have led to aromatase inhibitors replacing tamoxifen as the standard of care for breast cancer treatment.

Breast Cancer

Today, among women in the United States, breast cancer remains the most frequent diagnosed cancer. One in 8 women in the United States is at risk of developing breast cancer. Age, family history, diet, and genetic factors have been identified as risk factors for breast cancer. Breast cancer is the second leading cause of death among women.

HER2/neu Positive Breast Cancer

Cancers associated with overexpression of HER2/neu include breast, ovarian, endometrial, prostate, gastric, salivary gland, pancreatic, colorectal, oral and non-small cell lung cancers. Breast cancer has been a focus of anti-HER2/neu treatments.

Approximately 25-30 percent of breast cancers have an amplification of the HER2/neu gene or overexpression of its protein product. Overexpression of this receptor in breast cancer is associated with increased disease recurrence and worse prognosis.

Hormone Positive Cancer

Many breast cancers require the hormone estrogen to grow. In women who have had their menopause, the main source of estrogen is through the conversion of androgens into estrogens. As discussed above, this process is carried out by the aromatase enzyme.

Triple Negative Breast Cancer

In the treatment of triple negative breast cancer wherein the cancer is estrogen receptor-negative, progesterone receptor-negative and HER2-negative, compositions and therapies described herein may be combined with other therapeutic agents. Such agents include, by way of example only, cetuximab, paclitaxel, docetaxel, taxane formulations, for example, Abraxane® (ABI-007), Paclitaxel-Cremophor EL, Paclitaxel poliglumex, and Paclitaxel injectable emulsion (PIE). These combinations may be advantageous when the cancer association with HER2 overexpression is present but undetected due to technical limitations in tests employed in quantifying HER 2 expression.

Hormonal therapies are the mainstay of treatment of estrogen receptor positive (ER+) breast cancer (BC). Due to both the clinical activity and the overall favorable side effect profile and tolerance of hormonal agents, the standard of care typically involves sequencing of hormonal agents until either the development of resistance and/or visceral crises necessitate switching to chemotherapy. In post-menopausal women the aromatase inhibitors (AI) are a preferred class of anti-estrogen therapy that functions by blocking endogenous estrogen synthesis. Exemestane is a steroidal AI which irreversibly binds and inactivates the aromatase enzyme with demonstrated efficacy in the metastatic setting after progression on a non-steroidal AI, NSAI; i.e. letrozole or anastrozole (Chia S, Gradishar W, Mauriac L, et al: Double-blind, randomized placebo controlled trial of fulvestrant compared with exemestane after prior nonsteroidal aromatase inhibitor therapy in postmenopausal women with hormone receptor-positive, advanced breast cancer: results from EFECT. J Clin Oncol 26:1664-1670, 2008).

The development of resistance to hormone therapies in advanced BC represents a significant challenge. Putative mechanisms of resistance include estrogen-independent growth, hypersensitivity to low estrogen concentrations, cyclin D1 over-expression, constitutive nuclear factor kappa B (NFκB) activation, up-regulation of growth factor signaling pathways and down-regulation of estrogen receptor alpha (ERα) expression. These pathways and mechanisms provide potential targets for therapeutic interventions. Entinostat is a novel, oral inhibitor of histone deacetylases (HDAC), with high specificity towards class 1 HDACs and a unique pharmacological profile allowing for weekly dosing. HDAC inhibition leads to elevated protein lysine acetylation in tumor and peripheral blood cells serving as a surrogate potential pharmacodynamic marker of activity. Entinostat's class 1 specificity distinguishes it from the United States (US) Food and Drug Administration (FDA)-approved HDAC inhibitors (HDACi) vorinstat (Zolinza®) and romidepsin (Istodax®). Preclinically, entinostat has demonstrated inhibition of ERα positive tumor growth and restoration of hormone sensitivity as a result of down-regulation of estrogen-independent growth factor signaling pathways, normalization of ERα levels and increases in aromatase enzyme levels. (Sabnis G J, Goloubeva O, Chumsri S, et al: Functional activation of the estrogen receptor-α and aromatase by the HDAC inhibitor entinostat sensitizes ER-negative tumors to letrozole. Cancer Res 71:1893-903, 2011; Sabnis G J, Kazi A, Goloubeva O, Brodie A M H. HDAC Inhibitor Entinostat Restores Responsiveness of Letrozole Resistant MCF-7Ca Xenografts to AIs through Modulation of Her-2. Presented at the 33rd Annual San Antonio Breast Cancer Symposium, San Antonio, Tex., Dec. 8-12, 2010). The particular clinical trial results described herein demonstrate that combining entinostat with exemestane in ER+ breast cancers inhibits mechanisms of hormone therapy resistance thereby sensitizing cells to anti-estrogen therapy with exemestane.

Additional Therapy

Available additional treatments for breast cancer that may be advantageously employed in combination with the therapies disclosed herein include, without limitation, radiation therapy, chemotherapy, antibody therapy, and tyrosine kinase inhibitors as adjuvant therapy.

Radiation therapy is a cancer treatment that uses high-energy x-rays or other types of radiation to kill cancer cells or keep them from growing. Chemotherapy is a cancer treatment that uses drugs to stop the growth of cancer cells, either by killing the cells or by stopping them from dividing. When chemotherapy is taken by mouth or injected into a vein or muscle, the drugs enter the bloodstream and can reach cancer cells throughout the body (systemic chemotherapy). When chemotherapy is placed directly into the spinal column, an organ, or a body cavity such as the abdomen, the drugs mainly affect cancer cells in those areas (regional chemotherapy). The way the chemotherapy is given depends on the type and stage of the cancer being treated.

Different chemotherapeutic agents are known in the art for treating breast cancer. Cytoxic agents used for treating breast cancer include doxorubicin, cyclophosphamide, methotrexate, 5-fluorouracil, mitomycin C, mitoxantrone, paclitaxel, taxane formulations such as by way of example only, Abraxane® (ABI-007), Paclitaxel-Cremophor EL, Paclitaxel poliglumex, and Paclitaxel injectable emulsion (PIE), gemcitabine, docetaxel, capecitabine and epirubicin.

Other chemotherapy against breast cancer includes treatment with one or more of bendamustine, carboplatin (for example, Paraplatin®), carmustine (for example, BCNU®), chlorambucil (for example, Leukeran®), cisplatin (for example, Platinol®), cyclophosphamide injection (for example, Cytoxan®), oral cyclophosphamide (for example, Cytoxan®), dacarbazine (for example, DTIC®), ifosfamide (for example, Ifex®), lomustine (for example, CCNU®), mechlorethamine (for example, nitrogen mustard, Mustargen®), melphalan (for example, Alkeran®), procarbazine (for example, Matulane®), bleomycin (for example, Blenoxane®), doxorubicin (for example, Adriamycin®, Rubex®), epirubicin, Idarubicin (for example, Idamycin®), mitoxantrone (for example, Novantrone®), gemcitabine (for example, Gemzar®), oral mercaptopurine (for example, Purinethol®). methotrexate, pentostatin IV (for example, Nipent®), oral thioguanine (for example, Lanvis®), oral etoposide (for example, VP-16, VePesid®, Etopophos)—etoposide IV (for example, VP-16, VePesid®, Etopophos), vinblastine (for example, Velban®), vincristine (for example, Oncovin®), vinorelbine (for example, Navelbine®), dexamethasone (for example, Decadron®), methylprednisolone (for example, Medrol®), and prednisone (for example, Deltasone®).

Monoclonal antibody therapy is a cancer treatment that uses antibodies made in the laboratory, from a single type of immune system cell. These antibodies can identify substances on cancer cells or normal substances that may help cancer cells grow. The antibodies attach to the substances and kill the cancer cells, block their growth, or keep them from spreading. Monoclonal antibodies are given by infusion. They may be used alone or to carry drugs, toxins, or radioactive material directly to cancer cells. Monoclonal antibodies are also used in combination with chemotherapy as adjuvant therapy.

Trastuzumab (Herceptin®) is a monoclonal antibody that blocks the effects of the growth factor protein HER2, which transmits growth signals to breast cancer cells.

Trastuzumab leads to clinical responses as a single agent and improves survival when added to chemotherapy for advanced HER2-positive breast cancer. However, some patients do not respond to trastuzumab, and most eventually develop clinical resistance. Mechanisms of intrinsic and acquired trastuzumab resistance are poorly understood. One study which utilized a cell line-based approach to delineate genetic and protein alterations associated with resistance has been reported (D. Tripathy et al Journal of Clinical Oncology, 2005 Vol 23, No 16S, 3121). These researchers studied two HER2-positive breast cancer cell lines (BT474 and SKBR3) that were serially passaged in the presence of trastuzumab until in vitro resistance was documented. Resistant cell lines emerged after 12 months and exhibited a 3-fold more rapid growth rate in the absence of trastuzumab. Following trastuzumab exposure, $G_0/G_1$ arrest was observed in sensitive compared to resistant cells (84 vs. 68%), with fewer cells in S-phase (3 vs. 14%). Resistant cell lines exhibited fewer changes in gene expression with trastuzumab as well as upregulation of the chemokine receptor CXCR4 and mitotic checkpoint regulators, and downregulation of PTEN compared to sensitive cells.

Additional, illustrative, treatments that may be advantageously combined with the compositions and therapies disclosed herein may include, without limitation, administration of agents including, but not limited to lapatinib, alone or in combination with capecitabine, docetaxel, epirubicin, epothilone A, B or D, goserelin acetate, paclitaxel, pamidronate, bevacizumab, or trastuzumab.

In some embodiments, the additional therapy comprises chemotherapy comprising administering to the subject one or more of doxorubicin, cyclophosphamide, paclitaxel, lapatinib, capecitabine, trastuzumab, bevacizumab, gemcitabine, eribulin, or nab-paclitaxel.

Oral Formulations

Oral formulations containing the active pharmaceutical ingredients described herein may comprise any conventionally used oral forms, including: tablets, capsules, pills, troches, lozenges, pastilles, cachets, pellets, medicated chewing gum, granules, bulk powders, effervescent or non-effervescent powders or granules, solutions, emulsions, suspensions, solutions, wafers, sprinkles, elixirs, syrups, buccal forms, and oral liquids. Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. In some embodiments are surface modifying agents which include nonionic and anionic surface modifying agents. For example, surface modifying agents include, but are not limited to, poloxamer 188, benzalkonium chloride, calcium stearate, cetostearyl alcohol, cetomacrogol emulsifying wax, sorbitan esters, colloidal silicon dioxide, phosphates, sodium dodecylsulfate, magnesium aluminum silicate, and triethanolamine. Oral formulations herein may utilize standard delay or time release formulations to alter the absorption of the active compound(s). The oral formulation may also consist of administering the active ingredient in water or a fruit juice, containing appropriate solubilizers or emulsifiers as needed.

Oral Administration

As described herein, the combination therapy described herein can be given simultaneously or can be given in a staggered regimen, with entinostat being given at a different time during the course of chemotherapy than the aromatase inhibitor. This time differential may range from several minutes, hours, days, weeks, or longer between administrations of the two compounds. Therefore, the term combination does not necessarily mean administered at the same time or as a unitary dose, but that each of the components are administered during a desired treatment period. The agents may also be administered by different routes. As is typical for chemotherapeutic regimens, a course of chemotherapy may be repeated several weeks later, and may follow the same timeframe for administration of the two compounds, or may be modified based on patient response.

In other embodiments, the pharmaceutical compositions provided herein may be provided in solid, semisolid, or liquid dosage forms for oral administration. As used herein, oral administration also include buccal, lingual, and sublingual administration. Suitable oral dosage forms include, but are not limited to, tablets, capsules, pills, troches, lozenges, pastilles, cachets, pellets, medicated chewing gum, granules, bulk powders, effervescent or non-effervescent powders or granules, solutions, emulsions, suspensions, solutions, wafers, sprinkles, elixirs, and syrups. In addition to the active ingredient(s), the pharmaceutical compositions may contain one or more pharmaceutically acceptable carriers or excipients, including, but not limited to, binders, fillers, diluents, disintegrants, wetting agents, lubricants, glidants, coloring agents, dye-migration inhibitors, sweetening agents, and flavoring agents.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, Panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The binder or filler may be present from about 50 to about 99% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of disintegrant in the pharmaceutical compositions provided herein varies upon the type of formulation, and is readily discernible to those of ordinary skill in the art. The pharmaceutical compositions provided herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W.R. Grace Co., Baltimore, Md.) and CAB-O-SIL® (Cabot Co. of Boston, Mass.); and mixtures thereof. The pharmaceutical compositions provided herein may contain about 0.1 to about 5% by weight of a lubricant.

Suitable glidants include colloidal silicon dioxide, CAB-O-SIL® (Cabot Co. of Boston, Mass.), and asbestos-free talc. Coloring agents include any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Flavoring agents include natural flavors extracted from plants, such as fruits, and synthetic blends of compounds which produce a pleasant taste sensation, such as peppermint and methyl salicylate. Sweetening agents include sucrose, lactose, mannitol, syrups, glycerin, and artificial sweeteners, such as saccharin and aspartame. Suitable emulsifying agents include gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suspending and dispersing agents include sodium carboxymethylcellulose, pectin, tragacanth, Veegum, acacia, sodium carbomethylcellulose, hydroxypropyl methylcellulose, and polyvinylpyrolidone. Preservatives include glycerin, methyl and propylparaben, benzoic add, sodium benzoate and alcohol. Wetting agents include propylene glycol monostearate, sorbitan monooleate, diethylene glycol monolaurate, and polyoxyethylene lauryl ether. Solvents include glycerin, sorbitol, ethyl alcohol, and syrup. Examples of non-aqueous liquids utilized in emulsions include mineral oil and cottonseed oil. Organic acids include citric and tartaric acid. Sources of carbon dioxide include sodium bicarbonate and sodium carbonate.

It should be understood that many carriers and excipients may serve several functions, even within the same formulation.

In further embodiments, the pharmaceutical compositions provided herein may be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenylsalicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms may be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein may be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

In other embodiments, the pharmaceutical compositions provided herein may be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquids or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde (the term "lower" means an alkyl having between 1 and 6 carbon atoms), e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or polyalkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations may further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical compositions provided herein for oral administration may be also provided in the forms of liposomes, micelles, microspheres, or nanosystems. Miccellar dosage forms can be prepared as described in U.S. Pat. No. 6,350,458.

In other embodiments, the pharmaceutical compositions provided herein may be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

The pharmaceutical compositions provided herein may be formulated as immediate or modified release dosage forms, including delayed-, sustained, pulsed-, controlled, targeted-, and programmed-release forms.

In further embodiments, the pharmaceutical compositions provided herein may be co-formulated with other active ingredients which do not impair the desired therapeutic action, or with substances that supplement the desired action.

EXAMPLES

Example 1a

A Phase 2, Randomized, Double-Blind, Study of Exemestane With and Without Entinostat in Postmenopausal Women With Locally Recurrent or Metastatic Estrogen Receptor-Positive Breast Cancer, Progressing on Treatment With a Non-Steroidal Aromatase Inhibitor The purpose of this study is to evaluate the safety and efficacy of entinostat in combination with exemestane in the treatment of advanced breast cancer.

Primary Outcome Measures are to compare the efficacy of exemestane alone with exemestane plus entinostat, as determined by the duration of progression free survival (PFS) measured from the date of randomization.

Secondary Outcome Measures are to compare objective response rate (ORR) and clinical benefit rate (CBR), and to evaluate the safety and tolerability of entinostat in combination with exemestane as measured by adverse events and laboratory safety parameters.

Study Design

| Arm | Assigned Interventions |
|---|---|
| 1: Experimental exemestane (Aromasin) 25 mg daily plus entinostat 5 mg PO once/week Interventions: Drug: entinostat Drug: exemestane | Drug: entinostat SNDX-275 5 mg tablet PO once/week Drug: exemestane exemestane 25 mg PO QD Other Name: Aromasin |
| 2: Placebo Comparator exemestane (Aromasin) 25 mg daily plus placebo PO once/week Intervention: Drug: exemestane | Drug: exemestane exemestane 25 mg PO QD Other Name: Aromasin |

Eligibility Criteria
Ages Eligible for Study: 18 Years and older
Genders Eligible for Study: Female
Accepts Healthy Volunteers: No
Inclusion Criteria:
    Postmenopausal female patients
    Histologically or cytologically confirmed ER+ breast cancer
    Relapsed or progressed on prior treatment with AI
    Metastatic disease must be measurable
    Patients receiving palliative radiation at the non-target lesions must have a 2 week wash out period following completion of the treatment prior to enrollment
    Patient may have had one prior chemotherapy as part of first line therapy as long as it was received before initiation of prior AI
    ECOG performance status: 0 to 1
    Laboratory parameters: a) Hemoglobin ≥9.0 g/dL; platelets ≥100.0×109/L; ANC ≥1.5×109/L without the use of hematopoietic growth factors b) Creatinine less than 2.5 times the upper limit of normal for the institution c) AST and ALT less than 2.5 times the upper limit of normal for the institution
    Able to understand and give written informed consent and comply with study procedures
Exclusion Criteria:
    Relapse on treatment with non-steroidal AI after less than 12 months for patients in the adjuvant setting
    Progressive disease after less than 3 months treatment with most recent AI for patients with metastatic disease
    Rapidly progressive, life-threatening metastases
    Any palliative radiotherapy to the measurable lesion
    Previous treatment with SNDX-275 or any other HDAC inhibitor including valproic acid
    Allergy to benzamides or inactive components of the study drug
    A history of allergies to any active or inactive ingredients of exemestane
    Any concomitant medical condition that precludes adequate study treatment compliance
    Patient is currently enrolled in (or completed within 30 days before study drug administration) another investigational drug study
    Patient is currently receiving treatment with valproic acid, Zolinza (vorinostat) or any other HDAC inhibitor or DNA methyltransferase inhibitor or any systemic anti-cancer treatment (with the exception of Lupron)

FIG. 1 provides a summary of the Phase 2 clinical trial indicating dosing schedule for the arms of treatment.

FIG. 2 provides a summary of inclusion criteria for the Phase 2 clinical trial detailing acceptable prior treatment.

Figure 3:
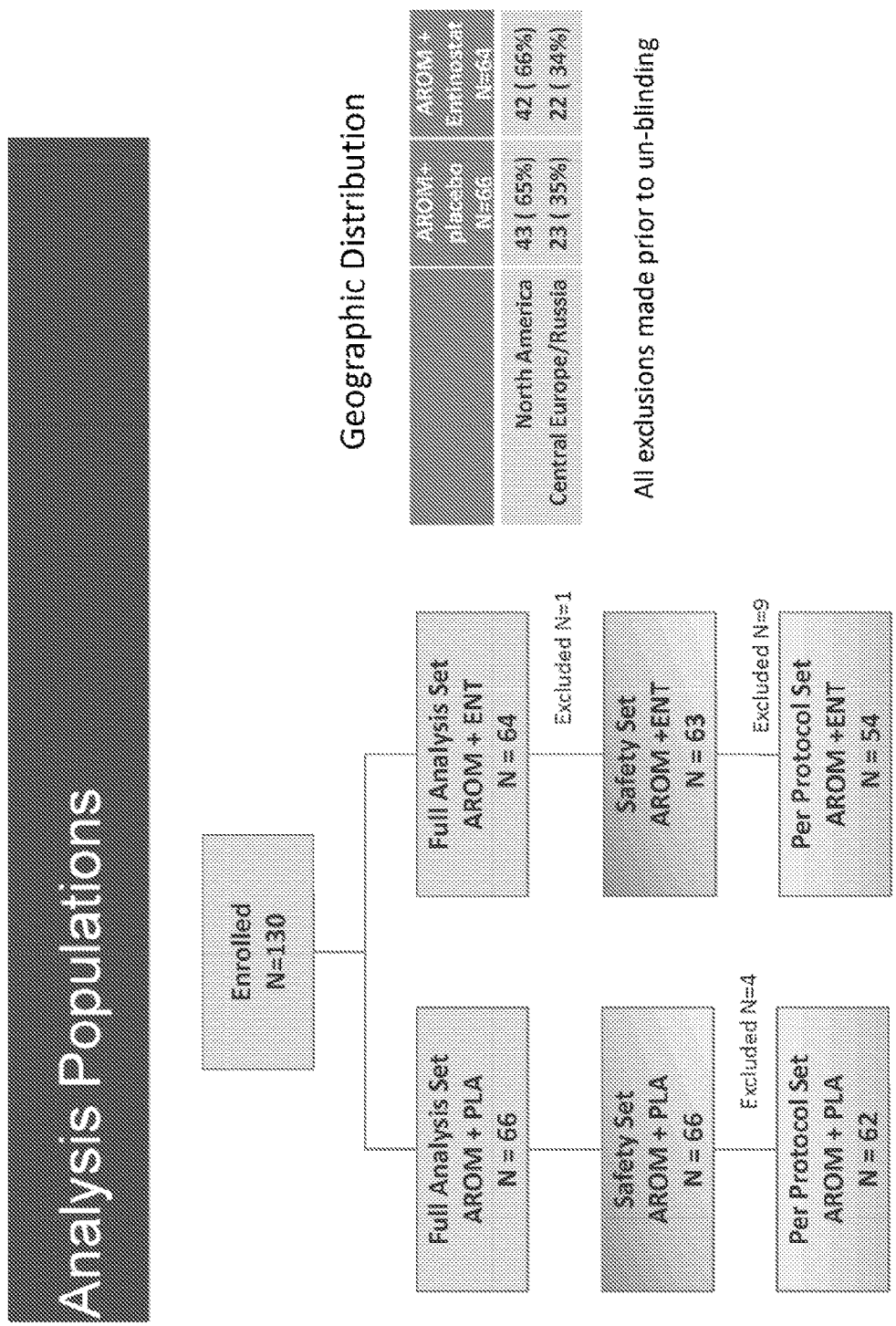
FIG. 3 provides an summary of the patient populations enrolled in the Phase 2 clinical trial.

FIG. 3 provides a summary of the patient populations enrolled in the Phase 2 clinical trial.

FIG. 4 provides a detailed analysis of the patient population enrolled in the Phase 2 clinical trial.

Figure 5:
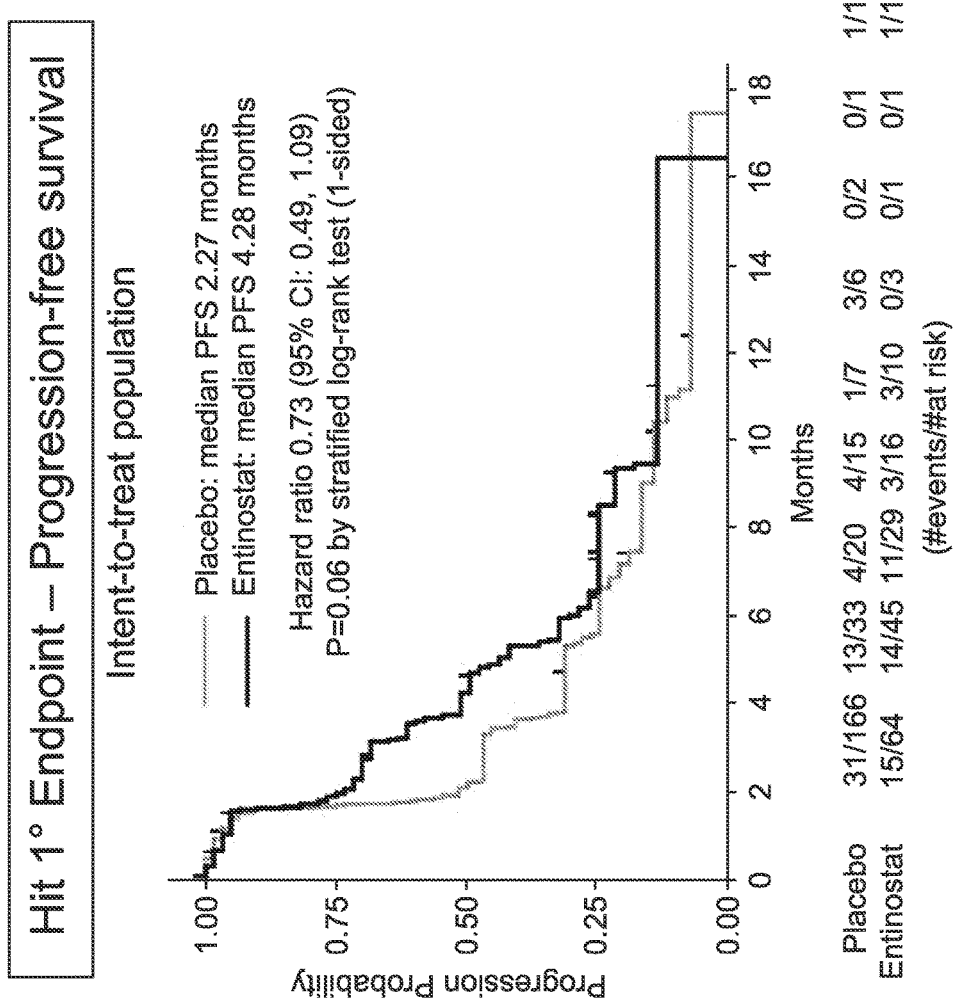
FIG. 5 provides a summary of progression-free survival during the in the Phase 2 clinical trial.

FIG. 5 provides a summary of progression-free survival during the in the Phase 2 clinical trial. The placebo arm (exemestane alone) had median PFS of 2.3 months, the treatment arm (exemestane and entinostat) had a median PFS 4.3 months.

FIG. 6 provides an analysis of benefit according to sub-group during the Phase 2 clinical trial. Hormone resistant patients showed the greatest benefit.

Figure 7:
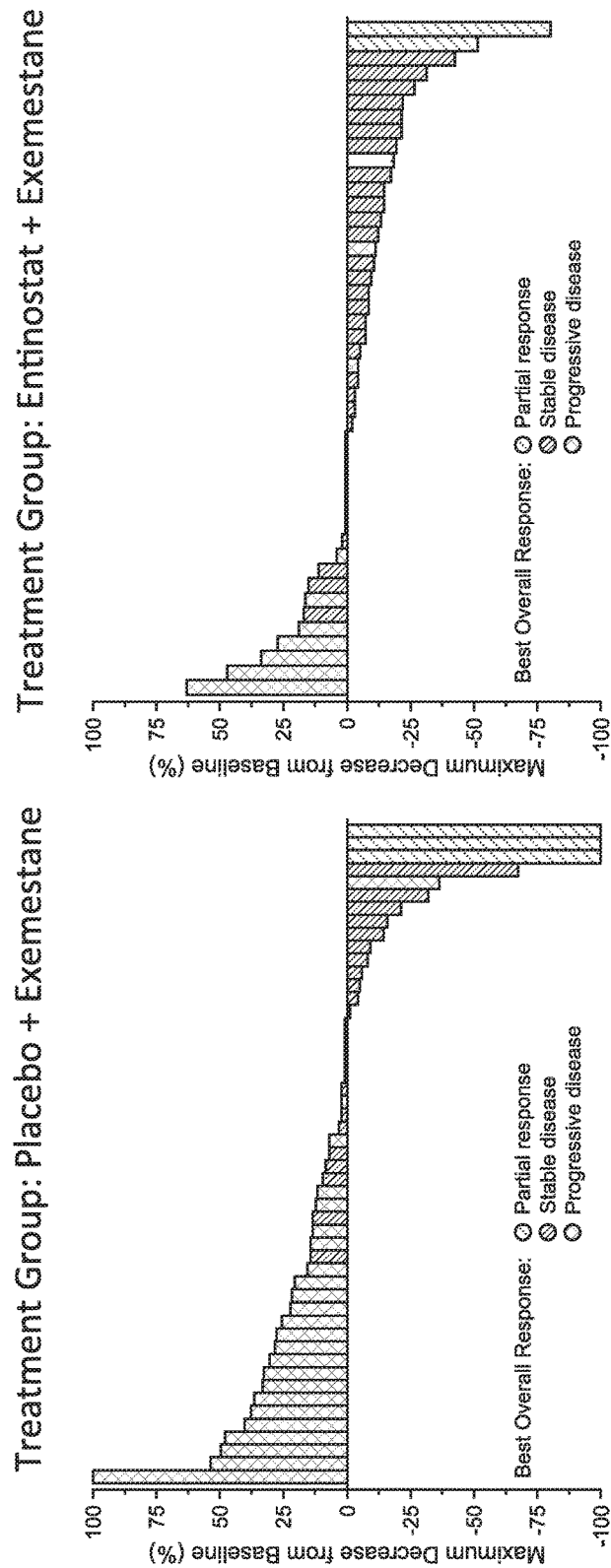
FIG. 7 provides an analysis of the change in tumor volume and type of response observed during the Phase 2 clinical trial.

FIG. 7 provides an analysis of the change in tumor volume and type of response observed during the Phase 2 clinical trial.

Figure 8:
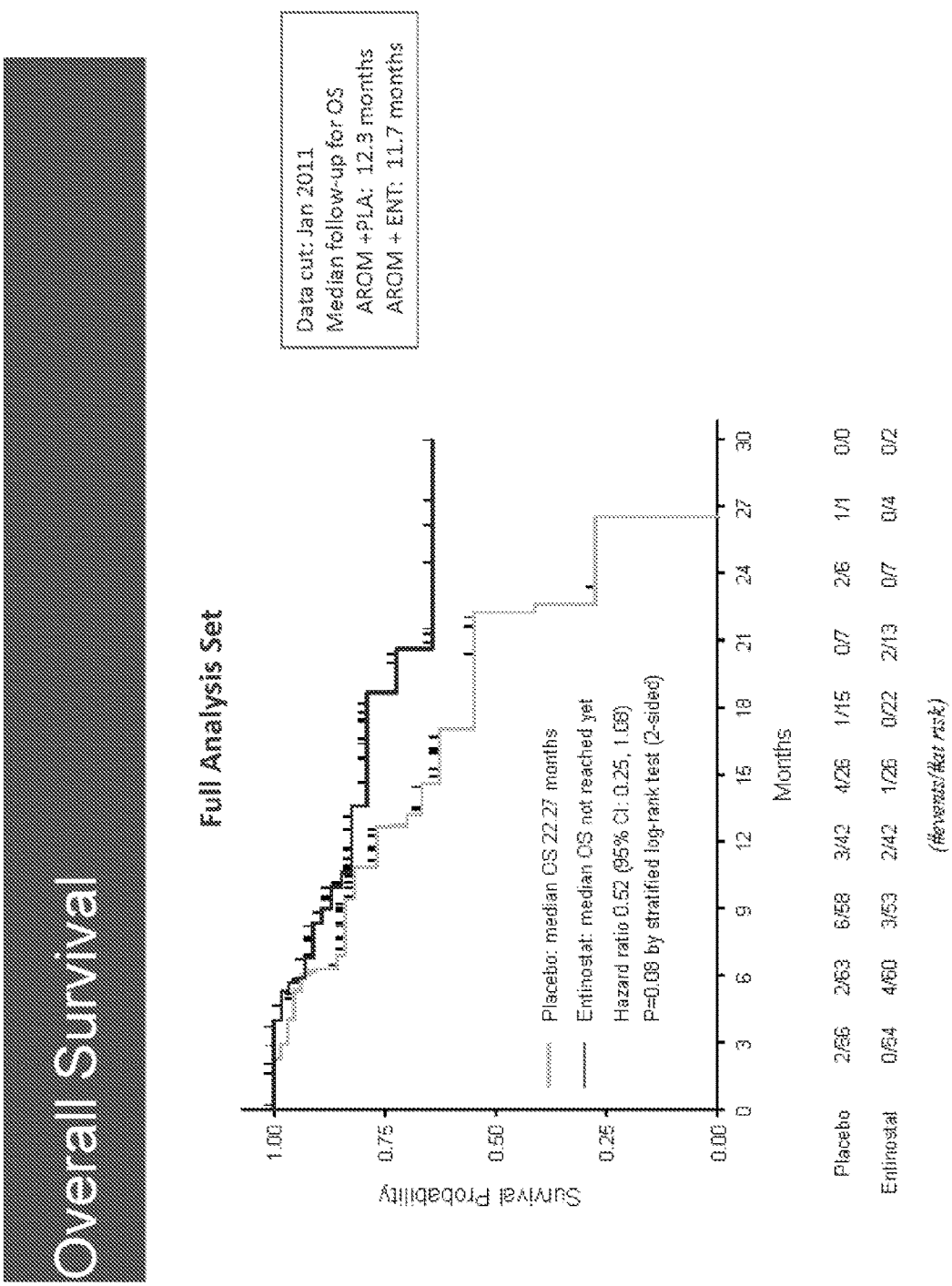
FIG. 8 provides a summary of overall survival observed during the Phase 2 clinical trial.

FIG. 8 provides a summary of overall survival observed during the Phase 2 clinical trial.

FIG. 9 provides a summary of adverse events observed during in the Phase 2 clinical trial. The combination of exemestane and entinostat was well tolerated.

FIG. 10 provides a general summary of the Phase 2 clinical trial.

The clinical trial described in Example 1a was a multicenter, randomized, double-blind, placebo-controlled, phase 2 study of exemestane with and without entinostat in 130 postmenopausal women with locally recurrent or metastatic estrogen receptor-positive breast cancer, progressing on treatment with the non-steroidal aromatase inhibitors anastrozole or letrozole. The primary endpoint of the study was progression-free survival. Other endpoints included objective response rate (ORR), clinical benefit rate (CBR), overall survival (OS) and safety and tolerability. All patients had received prior hormonal therapy (1 prior line 42%; >1 prior line 58%), and 33% had received prior chemotherapy in the advanced breast cancer setting. The results of this study with well-balanced arms included the following:

- In the intent-to-treat population progression-free survival was significantly longer (defined prospectively as 1-sided p<0.10) with exemestane plus entinostat than with exemestane plus placebo (4.28 versus 2.27 months, respectively; hazard ratio (HR)=0.73; p=0.06);
- In the intent-to-treat population, with a median follow-up of 18 months, overall survival was significantly longer with exemestane plus entinostat than with exemestane plus placebo (26.94 versus 20.33 months, respectively; hazard ratio (HR)=0.56; p=0.027);
- In the subset of entinostat patients with protein acetylation data (n=27), median PFS increased to over six months in the patients exhibiting protein lysine hyperacetylation;
- Entinostat combined with exemestane was well tolerated with the most frequent adverse events (AE) consisting of fatigue, gastrointestinal disturbances and hematologic abnormalities; and
- Serious AE rate was similar for exemestane plus entinostat (13%) and exemestane plus placebo (12%).

The study showed that patients who received entinostat with the hormone therapy exemestane lived longer without their disease getting worse than patients who received exemestane alone. Entinostat combined with exemestane prolonged progression-free survival, reducing the risk of disease progression by 27% and showing an improvement in overall survival for post-menopausal women with estrogen-receptor positive metastatic breast cancer. In a subset of patients evaluated for a pharmacodynamic measure of entinostat efficacy, this study demonstrated evidence of protein lysine hyperacetylation with positive clinical outcome.

Example 1b

In a 23-month patient follow up of the study described above in Example 1a, a multicenter, randomized, double-blind, placebo-controlled, phase 2 study of exemestane with and without entinostat in 130 patients with locally recurrent or metastatic estrogen receptor-positive breast cancer, the median overall survival of exemestane plus entinostat patients reached 26.9 months versus 19.8 months for exemestane plus placebo. This represents a 42% reduction (p=0.04) in the risk of dying for these patients. Earlier data from this study demonstrated a near doubling in the progression-free survival (PFS) (4.3 vs. 2.3 months) with exemestane plus entinostat and the identification of a subset of these patients whose median PFS reached 8.5 months.

The conclusion is that after two years of follow up the patients treated with entinostat and exemestane benefited from an additional seven months of overall survival. This study illustrates not only a progression-free survival advantage (4.3 months vs 2.3 months) but also an overall survival benefit for this combination which, coupled with an excellent safety and tolerability profile, provide evidence of benefit from this therapy.

Highlights of the data from the 23-month follow-up include:
- Overall survival: 26.9 months for exemestane+entinostat vs. 19.8 months for exemestane+placebo HR=0.58 (95% CI: 0.34, 0.97) p=0.04;
- Progression-free survival: 4.3 months for exemestane+entinostat vs. 2.3 months for exemestane+placebo HR=0.73 (95% CI: 0.49, 1.09) p=0.06; 1-sided significance prospectively defined as <0.10;
- Progression-free survival of 8.5 months for exemestane+entinostat in subset of patients with increased protein acetylaton vs. 2.8 months in non acetylators HR=0.32 (95% CI: 0.13, 0.79);
- Trend in improved progression-free survival in hormone-resistant vs. hormone-sensitive patients; and
- Exemestane combined with entinostat was well tolerated with the most frequent adverse events consisting of fatigue, gastrointestinal disturbances and hematologic abnormalities.

Example 1c

Confirmatory Phase 2 Study

Figure 11:
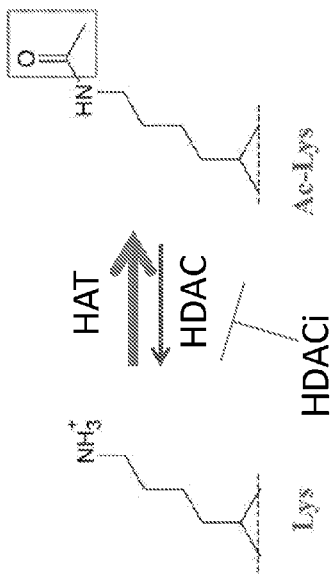
FIG. 11 provides an introduction to protein lysine acetylation.

The primary endpoint was progression-free survival (PFS). Peripheral blood mononuclear cells were collected in a subset of patients pre- and post-dose in cycle 1 for evaluation of protein lysine acetylation as a biomarker of entinostat activity (FIG. 11).

Patients and Methods

Figure 12:
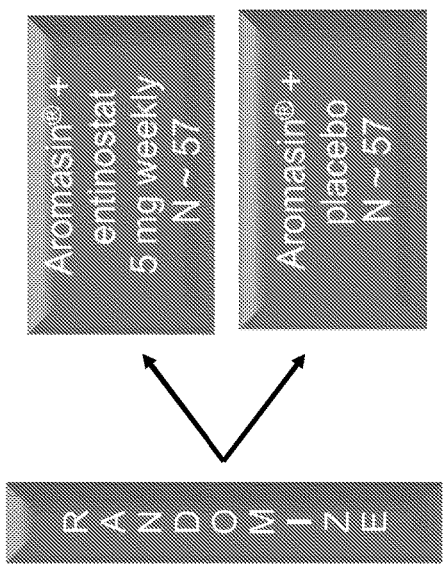
FIG. 12 provides a summary of the confirmatory Phase 2 study.
Figure 13:
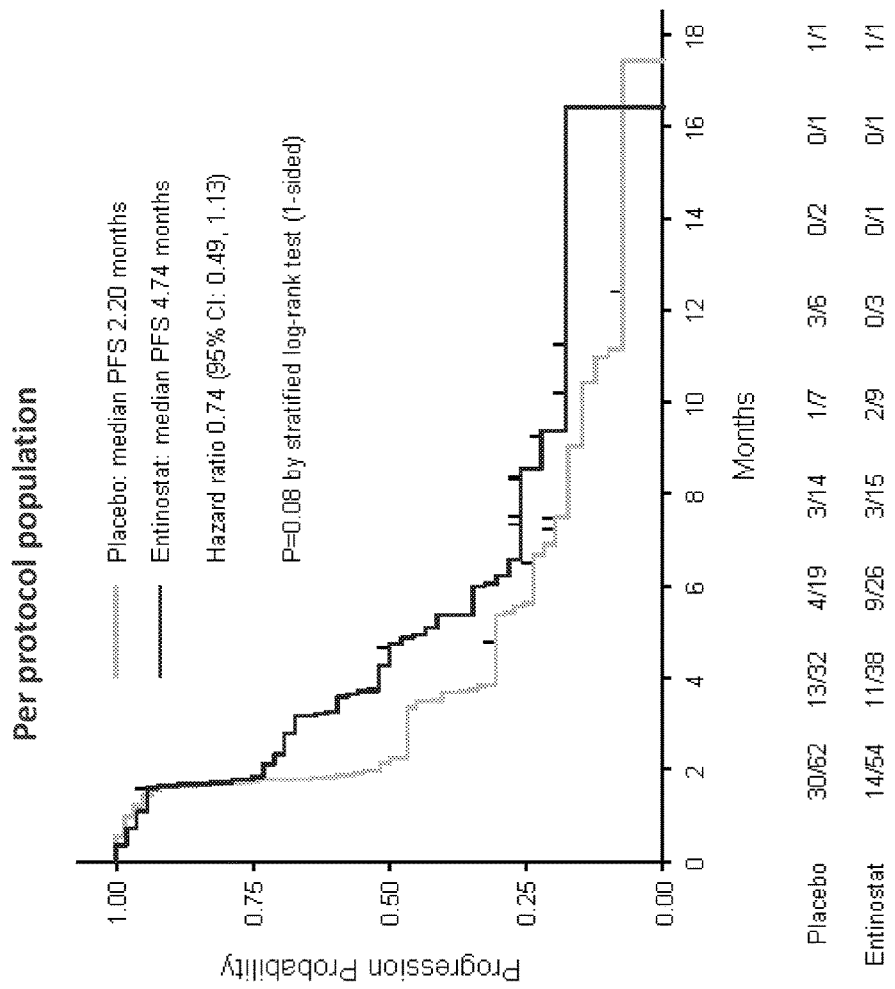
FIGS. 13, 14 and 15 provide an summary of the interim results of the confirmatory Phase 2 study.
Figure 14:
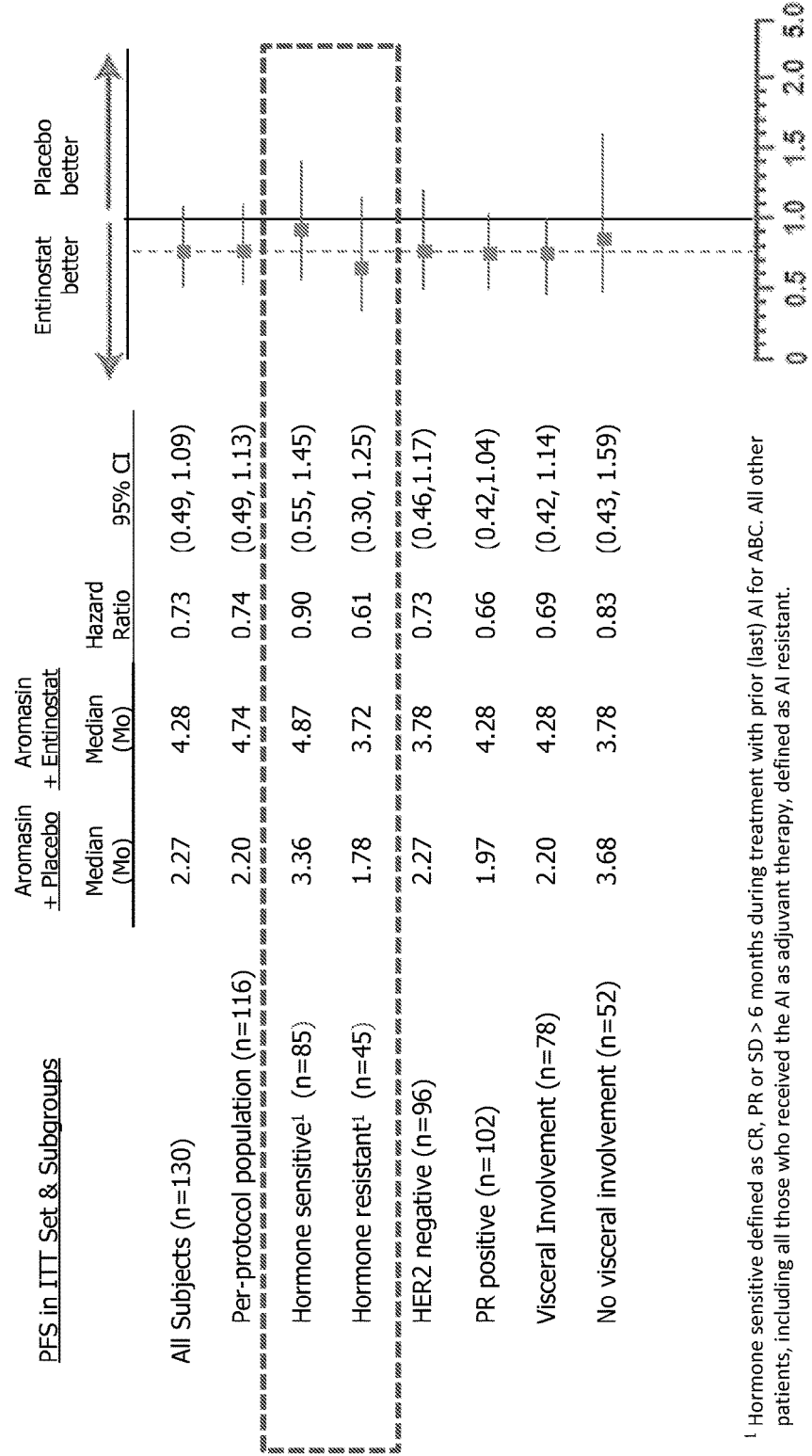
Figure 15:
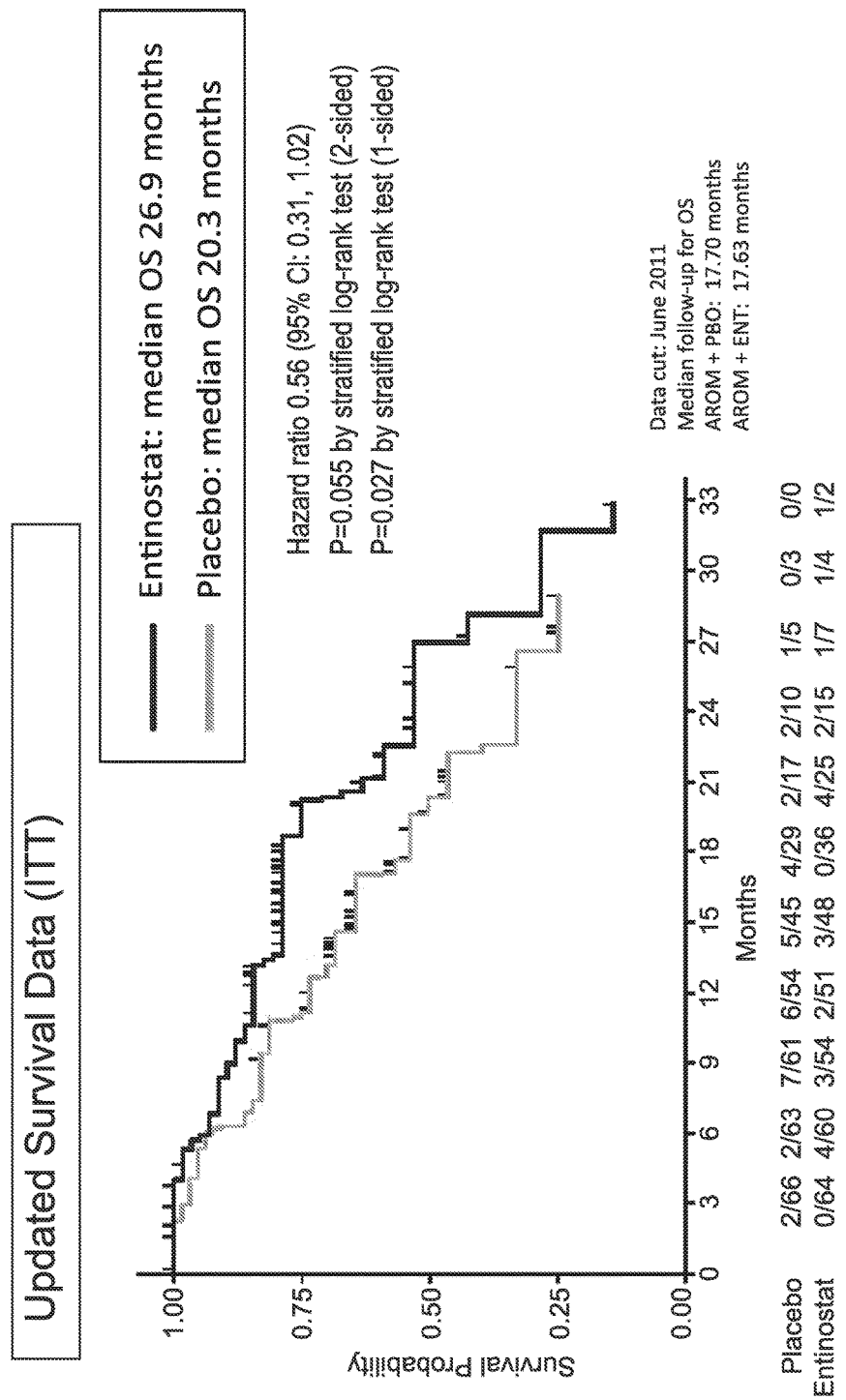

Study Design:

This was a Phase 2, randomized, double-blind, placebo-controlled study of exemestane±entinostat in patients with locally advanced or metastatic BC that had progressed on a NSAI (FIG. 12). One hundred thirty (130) patients were enrolled between June 2008 and July 2010 at 38 sites in North America, Central Europe, and Russia. All patients provided written informed consent. Patients were randomized in a 1:1 ratio using a blocked randomization scheme to exemestane plus entinostat (EE; n=64) or exemestane plus placebo (EP; n=66). Randomization was stratified by 1) prior NSAI treatment setting (adjuvant/metastatic); 2) metastases in bone only (yes/no); and 3) geographic region (North America/Central Europe and Russia). The randomization schedule was prepared and maintained by an independent statistical service provider. The protocol allowed for enrollment of approximately 20% of patients with non-measurable disease. Treatment with exemestane 25 mg by mouth (PO) once daily plus entinostat 5 mg or placebo PO once weekly continued until progressive disease (PD) or unacceptable toxicity.

Eligibility:

Postmenopausal women with ER+BC currently experiencing disease relapse or progression while receiving a NSAI were eligible. Patients either had 1) relapsed after adjuvant NSAI treatment administered for at least 12 months or 2) progressed after NSAI treatment administered for at least 3 months in the metastatic/advanced setting. One prior line of chemotherapy in the metastatic setting was permitted if given before the most recent NSAI. Within 4 weeks prior to starting study treatment, patients must have had at least 1 measurable lesion (≥20 mm by conventional techniques or ≥10 mm by spiral computed tomography [CT] scan), or with bone only metastases, a positive bone scan confirmed by magnetic resonance imaging (MRI) or positron emission tomography (PET)-CT. Additional requirements included, an Eastern Cooperative Oncology Group (ECOG) performance status of 0 or 1; adequate hematologic parameters; and creatinine, aspartate transaminase, and alanine transaminase <2.5 times the upper limit of normal. Patients with prior fulvestrant, exemestane, entinostat, or any other HDACi were excluded.

Procedures and Treatment:

Treatment cycles were 28 days in length. Patients were evaluated on Day (D) 1, D8, and D15 during Cycle (C) 1 and on D1 of all subsequent cycles. Peripheral blood samples were taken in a subset of patients pre- and post-dosing on D1, 8, or 15 of C1. Patient/disease response assessments were performed on D22 of C2 and every other cycle thereafter. After completing study treatment, patients entered into post-treatment follow-up for evaluation of overall survival and subsequent therapies. Patients were to be followed until death, withdrawal of consent, or study closure by the sponsor.

Assessments:

Safety Assessment:

Safety was assessed by adverse events (AEs), using the National Cancer Institute Common Terminology Criteria for Adverse Events, version 3.0, electrocardiograms, hematology and serum chemistries, ECOG performance status, and vital signs.

Efficacy Assessment:

Disease was evaluated using the Response Evaluation Criteria in Solid Tumors (RECIST), version 1.0. Contrast-enhanced CT scans were obtained at baseline, every other cycle for 12 months, and every third cycle thereafter. PD also was assessed by bone scan and clinical symptoms, as appropriate.

Endpoints:

The primary endpoint was PFS, defined as the number of months from randomization to documented PD or death due to any cause. Secondary endpoints included overall response (OR; complete response [CR]+partial response [PR]) and clinical benefit rates (CBR; OR+stable disease [SD] for ≥6 months). Overall Survival (OS) was an exploratory endpoint. Pre-defined subgroups included NSAI-sensitive: patients who had a CR, PR or SD for 6 months on their preceding NSAI therapy in the advanced setting or who relapsed at least 1 year after completion of a NSAI in the adjuvant setting and NSAI-resistant: all other patients.

Exploratory Pharmacodynamics:

Protein lysine acetylation was measured by multi-parameter flow cytometry in peripheral blood mononuclear cells (PBMCs; CD19+ B cells, CD3+ T cells, and CD14+ monocytes) collected pre and post-treatment on D1, D8, and D15 of C1 to explore the association with PFS.

Statistical Methods:

Chia, et al, reported a median PFS of 3.7 months with exemestane in the treatment of advanced BC demonstrating PD or recurrence following a NSAI. It was hypothesized that the addition of entinostat to exemestane would increase median PFS by 2.3 months (i.e., from 3.7 to 6.0 months), corresponding to a target hazard ratio (HR) of 0.62. For the primary analysis of PFS, a total of 77 progression events were required to detect such an improvement in the HR with ≥80% power, one-sided significance level of 0.10, and log-rank test. A total of 92 events were required for 85% power, and 112 events were required for 90% power. The initial type 1 and 2 error rates chosen for this study and the size of the targeted treatment effect are consistent with those proposed by Rubenstein, et al, and Korn, et al, for Phase 2 screening studies (Rubinstein L V, Korn E L, Freidlin B, et al: Design issues of randomized Phase 2 trials and a proposal for Phase 2 screening trials. J Clin Oncol 23:7199-7206, 2005; Korn E L, Arbuck S G, Pluda J M, et al: Clinical trial designs for cytostatic agents: are new approaches needed? J Clin Oncol 19:265-272, 2001).

PFS was summarized descriptively using the Kaplan-Meier method and reported based on 116 progression events as of March 2012. The HR was estimated from a stratified Cox proportional hazards model, with placebo serving as the reference in the calculation. The primary inferential comparison between groups was made using the log-rank test, stratified by the 3 randomization factors. For patients who died before documentation of PD, death date was used as the PD date. The duration of PFS was right-censored at the last disease assessment for patients who started non-protocol defined anticancer therapy, were lost to follow-up, or did not have documentation of PD. Multivariate Cox models were used to determine if the reduced hazard rate for PFS and OS attributed to entinostat treatment in the univariate model was still present after accounting for patient-, disease- and prior treatment-related factors. Efficacy analyses were performed using the Intention-to-treat Population, defined as all randomized patients. All reported p-values are one-sided and assessed using significance level of 0.10.

Safety analyses were performed using the Safety Population (all patients who received ≥1 dose of entinostat/placebo). Safety was assessed by an independent Data Safety Monitoring Board. All participating investigators and patients remain blinded to the assigned study treatment, as post-treatment follow-up for OS is continuing.

The association of PFS with degree of change in protein lysine acetylation from baseline in PBMCs was evaluated as an exploratory, post-hoc analysis in a subset of patients using the Cox proportional hazard model. Analyses in all 3 cell types (B cells, T cells, monocytes) was performed for consistency of results and to aid in selection of optimal cell type for analysis in future studies.

Results:

Patient Characteristics:

A total of 130 patients were randomized, 64 to EE and 66 to EP (FIGS. 3 and 12). Treatment groups were generally well balanced with the exception of visceral disease (53% EE versus 67% EP), median duration since initial BC diagnosis (7.9 years EE versus 4.6 years EP) and median duration since diagnosis of advanced BC (19.5 versus 17.2 months, respectively).

Of the 130 patients randomized, 85 (EE=45, EP=40) met the study-specified definition (see Endpoints) of NSAI-sensitive (1 had progressed after adjuvant NSAI, and 84 had progressed after metastatic NSAI) and 45 (EE=19, EP=26) were NSAI-resistant (18 had progressed after adjuvant NSAI, and 27 had progressed after metastatic NSAI).

Efficacy:

In the ITT population, median PFS was 4.3 months for EE versus 2.3 months for EP, with an HR=0.73; 95% CI 0.50, 1.07; p=0.055 (significant according to pre-specified design criteria). PFS benefit in favor of EE was consistent across all subgroups of prognostic importance, including patients with acquired resistance (NSAI-sensitive; HR=0.85; n=85) and primary resistance (NSAI-resistant; HR=0.47; n=45). The OR and CBR were similar for EE and EP (OR: 6.3% and 4.6%, respectively; CBR: 28.1% and 25.8%, respectively). Median OS was 28.1 months (EE) and 19.8 months (EP); HR 0.59; CI 0.36, 0.97; p=0.018 with the incidence of death at 42% for EE and 65% for EP. Multivariate analyses indicated the favorable PFS and OS outcomes for EE versus EP were preserved when adjusted for baseline factors, including visceral disease and duration of diagnosis of advanced BC.

Safety:

A total of 129 patients (EE=63, EP=66) were in the Safety Population. One EE patient withdrew from study prior to receiving treatment. Compared with EP, EE had a higher rate of AEs (95% versus 85%), Grade (G) 3 AEs (44% versus 23%), G4 AEs (6% versus 3%), AEs leading to dose modification (35% versus 6%), and AEs leading to study discontinuation (11% versus 2%), irrespective of study drug relationship. AEs leading to the majority of EE dose modifications included neutropenia (14%), thrombocytopenia (14%) and fatigue (6%). AEs leading to EE study discontinuation included nausea and vomiting (n=2), neutropenia (n=1), worsening weakening in extremities (n=1), hypoxia and radiation pneumonitis (n=1), fatigue (n=1), and mucositis (n=1). In EP 1 patient discontinued due to fatigue, anemia, thrombocytopenia and leukopenia. The entinostat AE profile was consistent with previous clinical experience. Most frequent (>15% of patients) AEs occurring in the EE group were fatigue, nausea, neutropenia, peripheral edema, vomiting, anemia, dyspnea, thrombocytopenia, decreased weight, diarrhea, and pain. Neutropenia was most commonly attributed to entinostat (13 of 19 cases; 68%). The incidence of serious AEs (EE=16%, EP=12%) was similar. Four (6%) EE patients each experienced a G4 AE, including fatigue, leukopenia, neutropenia, and hypercalcemia. One fatal AE occurred in, each treatment arm; the EE arm event was considered related to PD.

Figure 16:
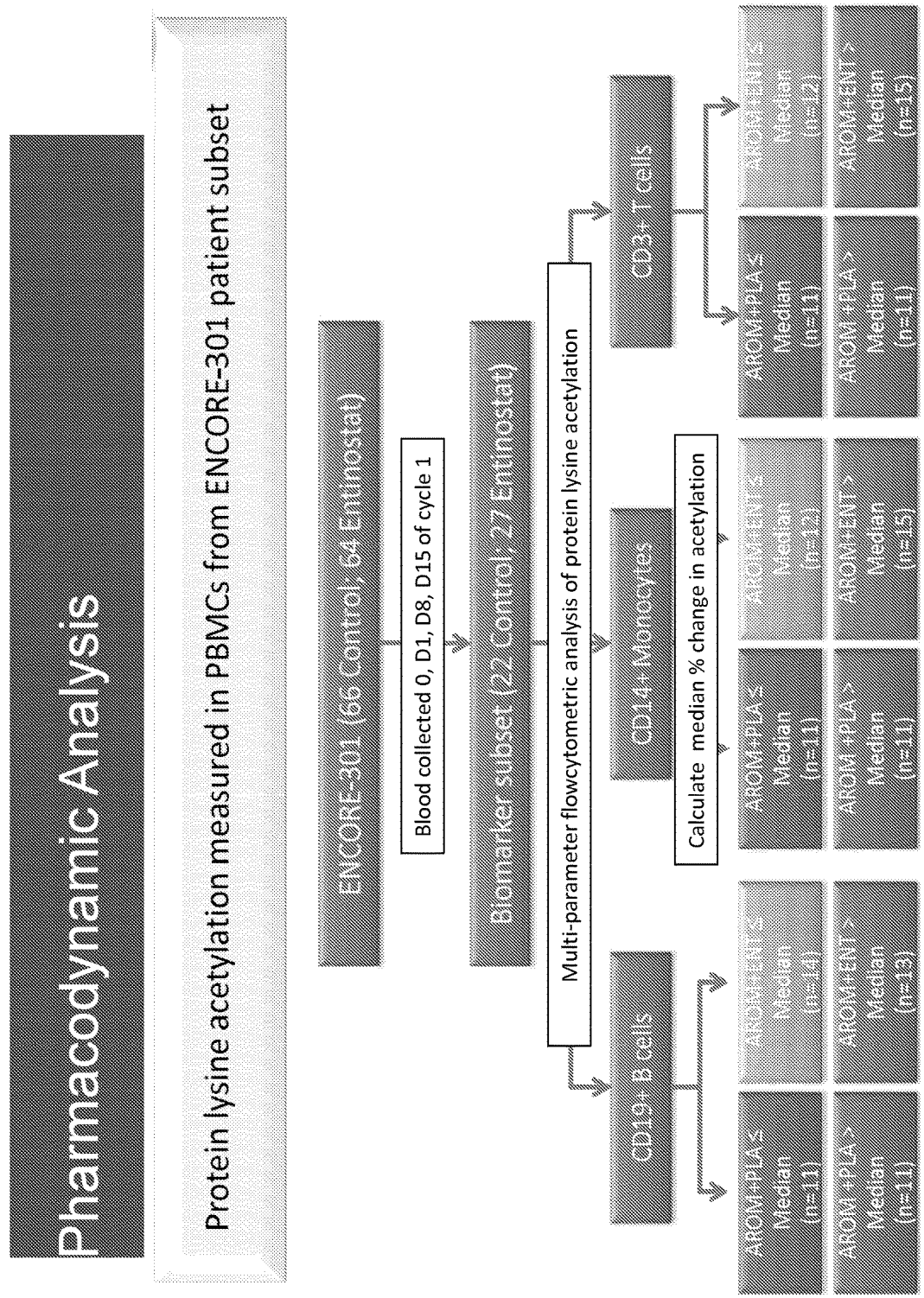
FIG. 16 provides a summary of the pharmacodynamic analysis performed to measure changes in protein lysine acetylation in the Phase 2 study.
Figure 17:
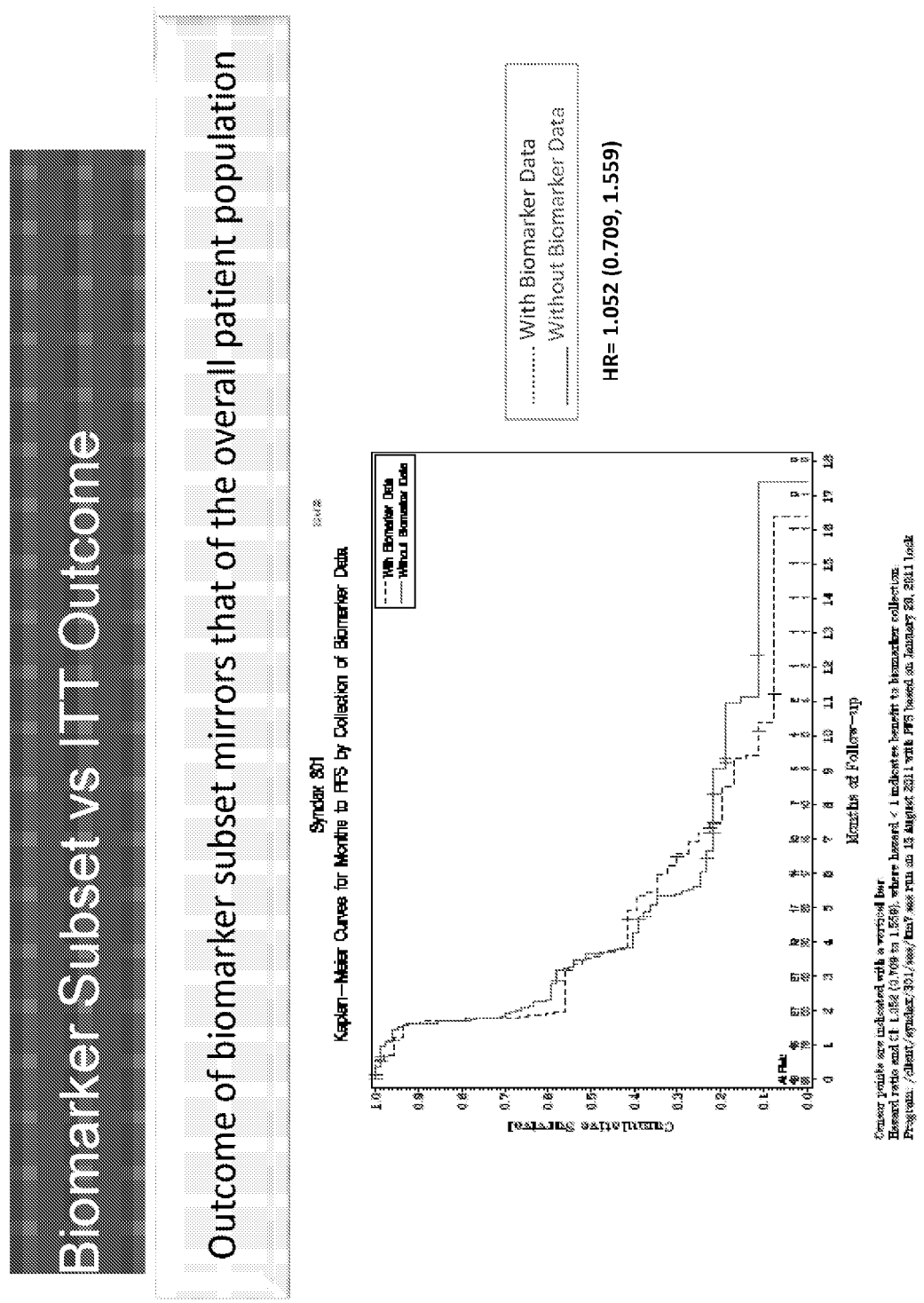
FIG. 17 provides a comparison between the biomarker patient population and the overall patient population in the Phase 2 study.

Biomarker Analysis:

Cycle 1 pre- and post-treatment samples were obtained in a subset of 49 patients (EE=27, EP=22) as shown in FIG. 16. Baseline characteristics were consistent with the overall study population (FIG. 17). Hyperacetylation in EE patients was associated with a prolonged median PFS consistent across all cell types tested (FIG. 18): 8.5 versus 2.7 months for low acetylators (HR=0.32, 95% CI 0.13, 0.79) (B cells); 6.6 versus 3.6 months for low acetylators (HR=0.44, 95% CI 0.18, 1.08) (T cells); and 6.2 versus 3.6 months for low acetylators (HR=0.50, 95% CI 0.21, 1.20) (monocytes). Plasma entinostat concentrations at time points used for acetylation evaluation were generally at or below the assay detection limit (<0.5 ng/mL), preventing correlation between entinostat concentration and acetylation status. The percent change in acetylation from baseline was determined based upon the last sample obtained. The degree of change in acetylation was then dichotomized into "high" (i.e., above the median or "hyperacetylators") and "low" (i.e., below the median) subgroups using a non-model based approach: patients with a change from baseline that was greater than or equal to the 50th percentile (median) of the overall distribution were assigned to the "high" group; patients with a change less than the 50th percentile were assigned to the "low" group. The cut-point for the analysis (50th percentile) was determined a priori, but was not based on findings from earlier studies.

Figure 19:
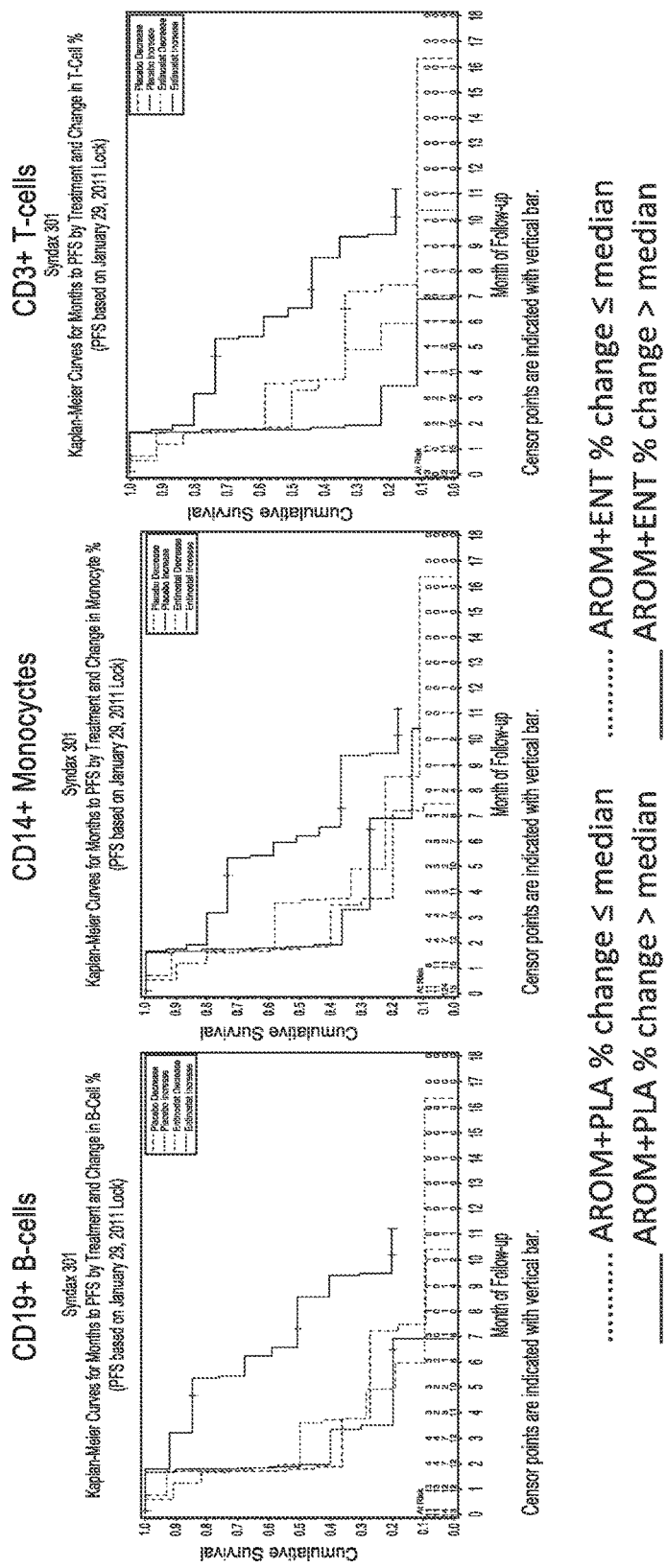
FIG. 19 provides a comparison of PFS to percent change of acetylation levels in each treatment arm in the Phase 2 study.
Figure 20:
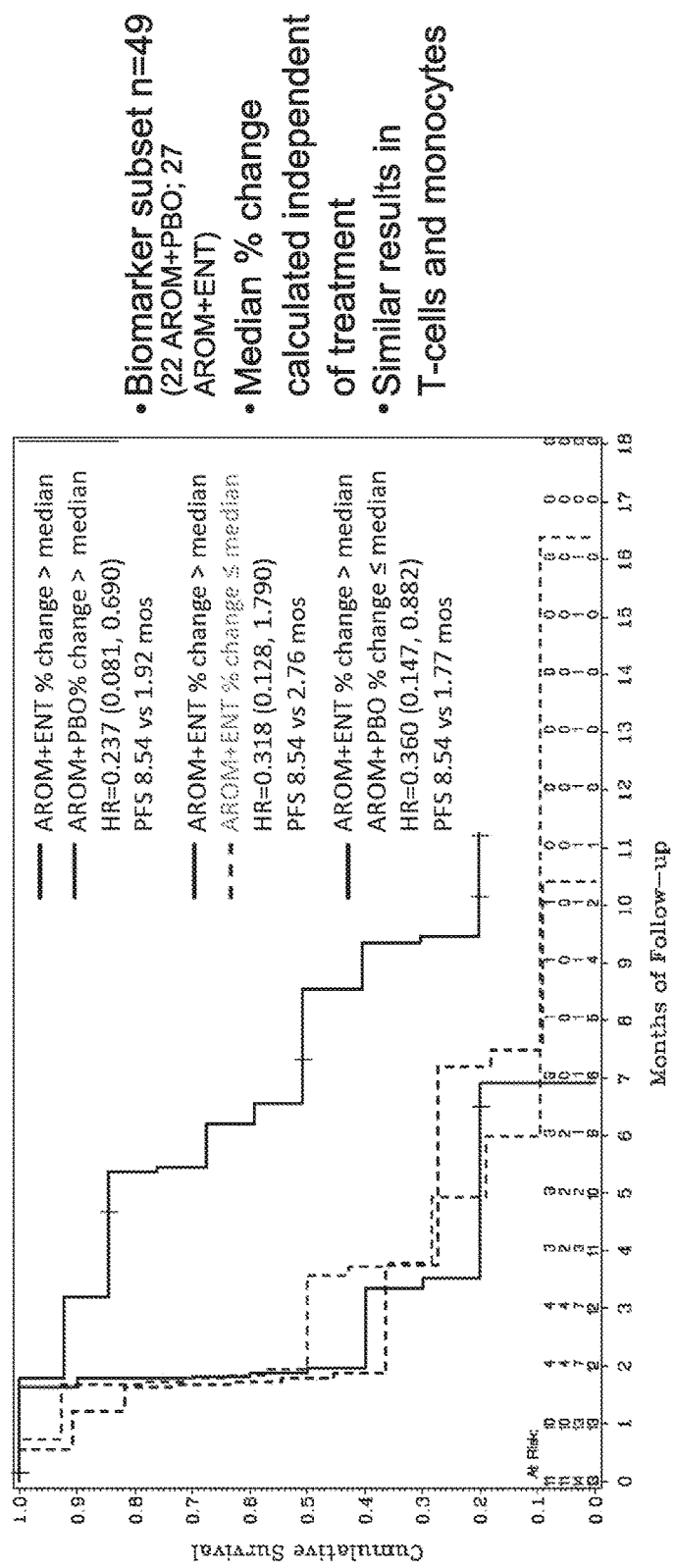
FIG. 20 provides a comparison of PFS to percent change of acetylation levels in each treatment arm in the Phase 2 study when the analysis is performed with B-cells.
Figure 24:
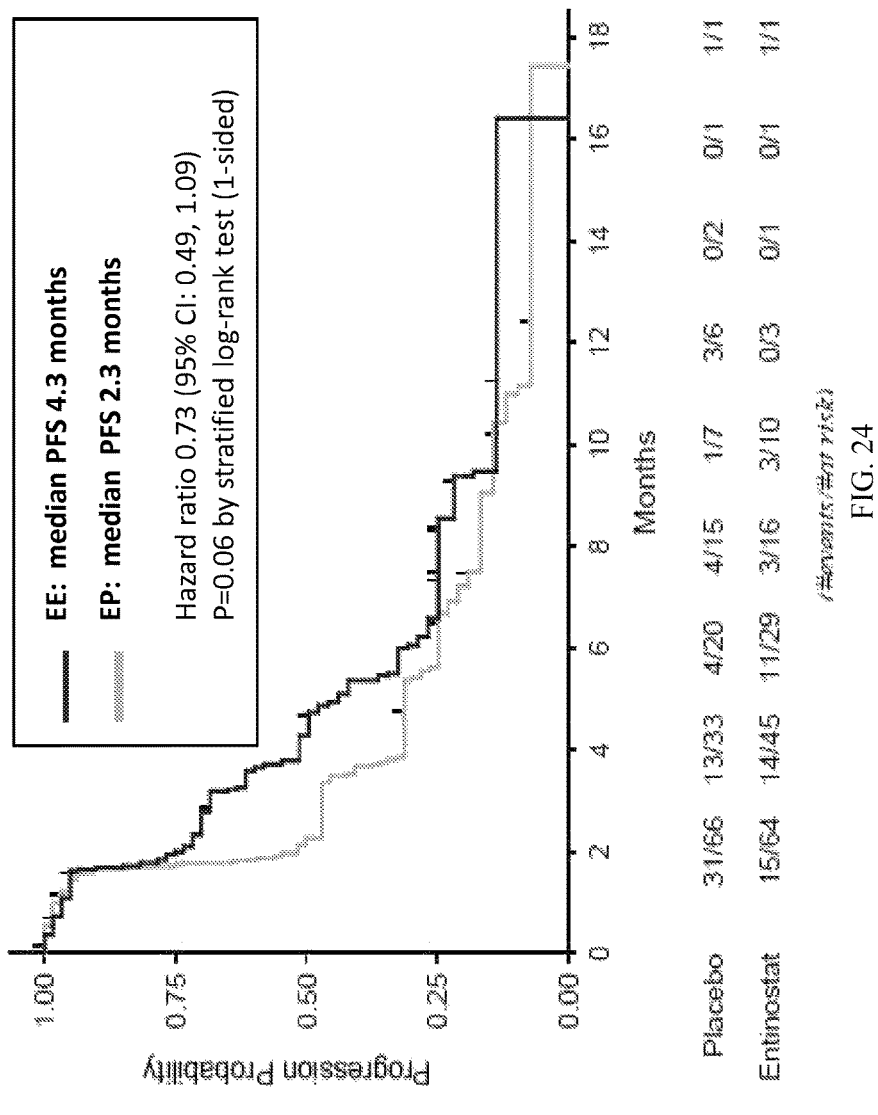
FIG. 24 provides an analysis for primary endpoint in the Phase 2 study.

Progression free survival was found to be greatest in the entinostat hyperacetylation group (FIG. 19). As shown in FIG. 20 for the B-cell analysis, EE high acetylating patients were associated with a PFS of 8.5 versus 1.9 for the EP high acetylating patients, 2.7 for the EE low acetylating patients, and 1.8 for the EP low acetylating patients. Similar results were seen in T-cell and monocyte analysis.

An analysis of adverse events versus acetylation status is provided in FIGS. 21 and 22.

Figure 25:
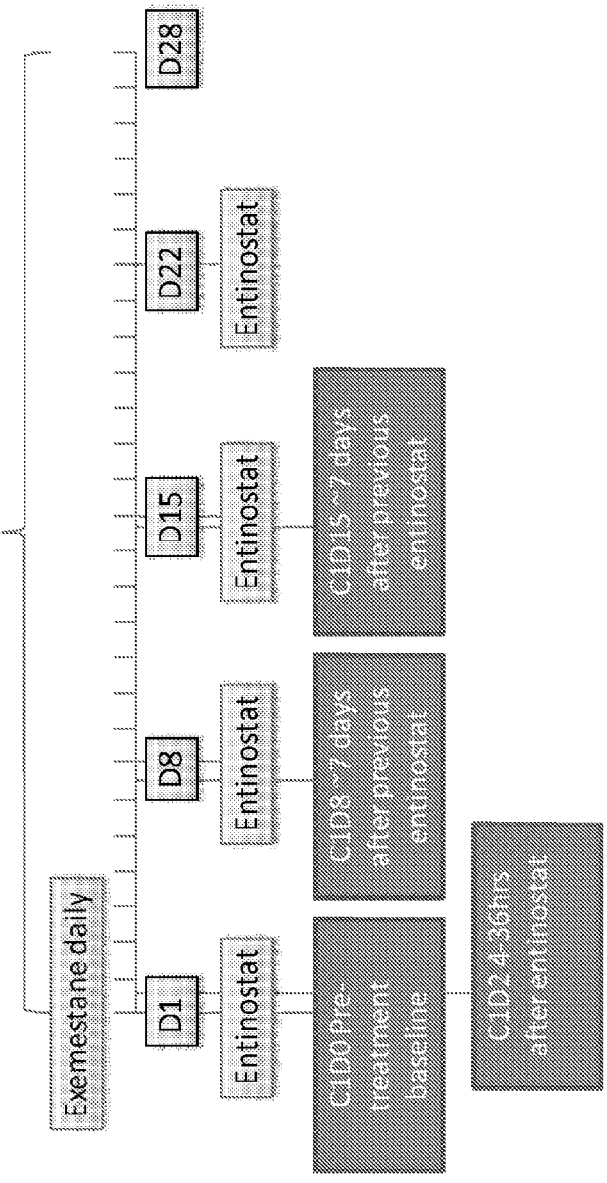
FIG. 25 provides a timeline for dosing and collection of samples in the pharmacodynamic analysis portion of the Phase 2 study.
Figure 26:
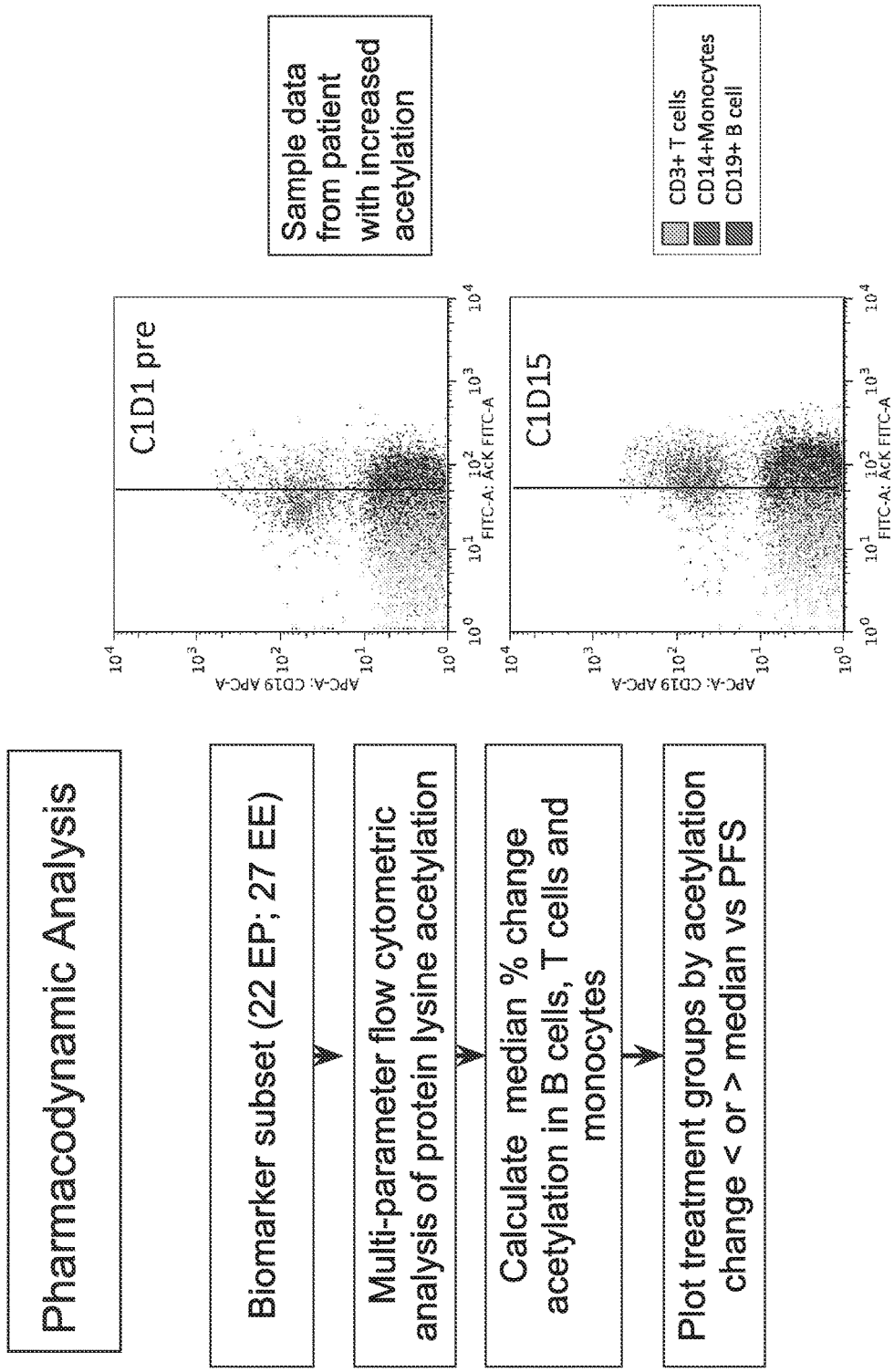
FIG. 26 provides a plot of treatment groups by acetylation change versus PFS.
Figure 27:
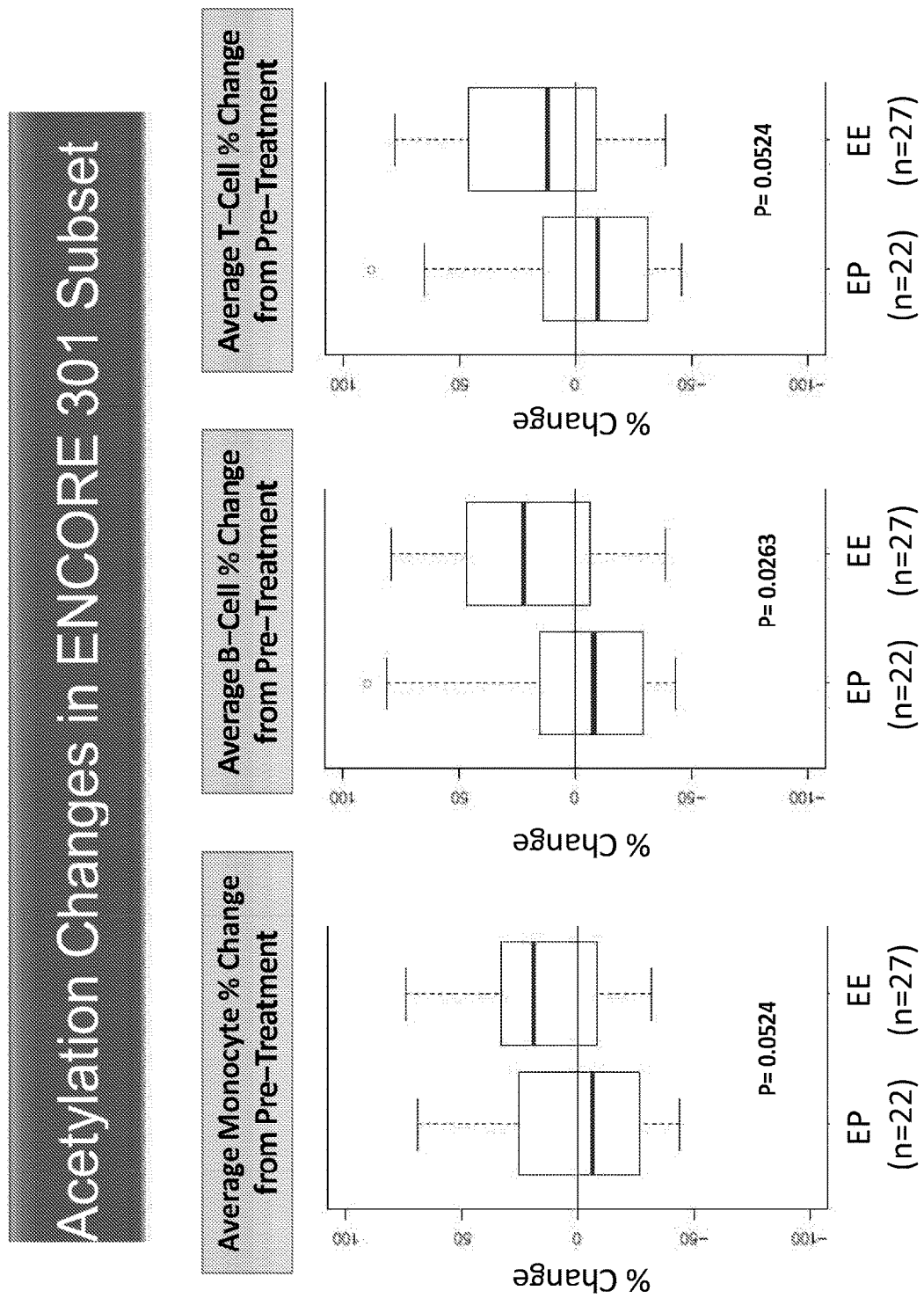
FIG. 27 provides a summary of the acetylation changes for the two treatment arms in the three different tissue types.
Figure 28:
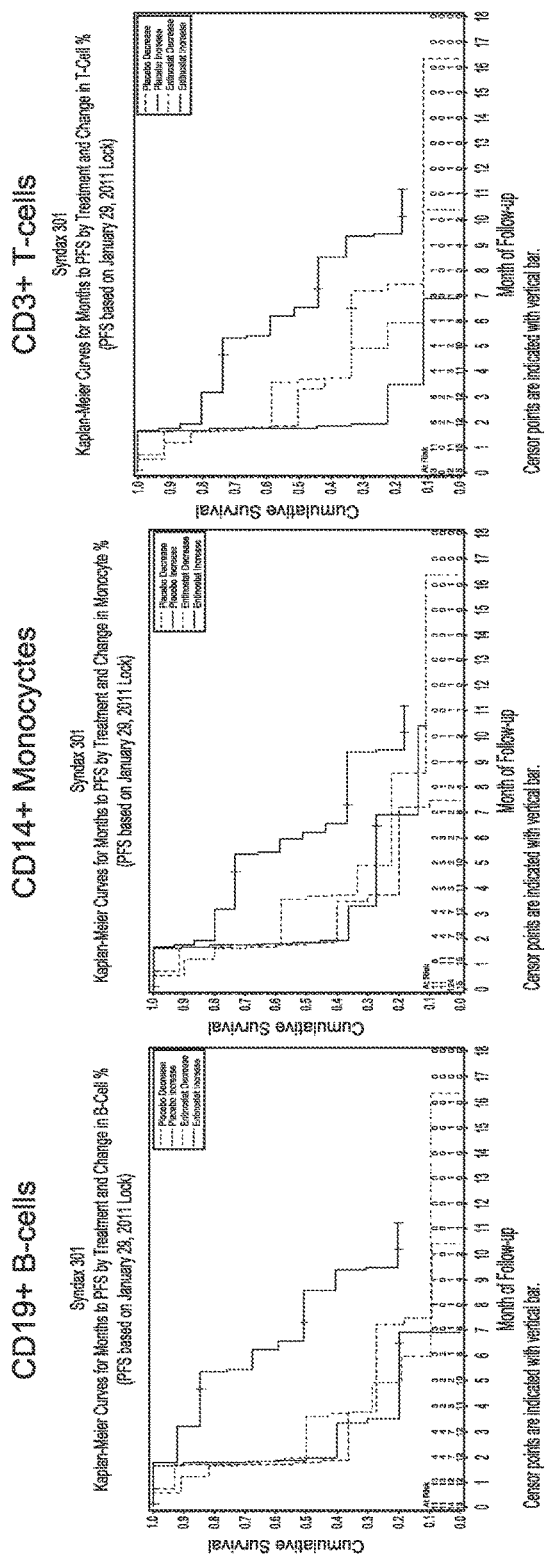
FIG. 28 provides a comparison of PFS to percent change of acetylation levels in each treatment arm in the Phase 2 study.
Figure 29:
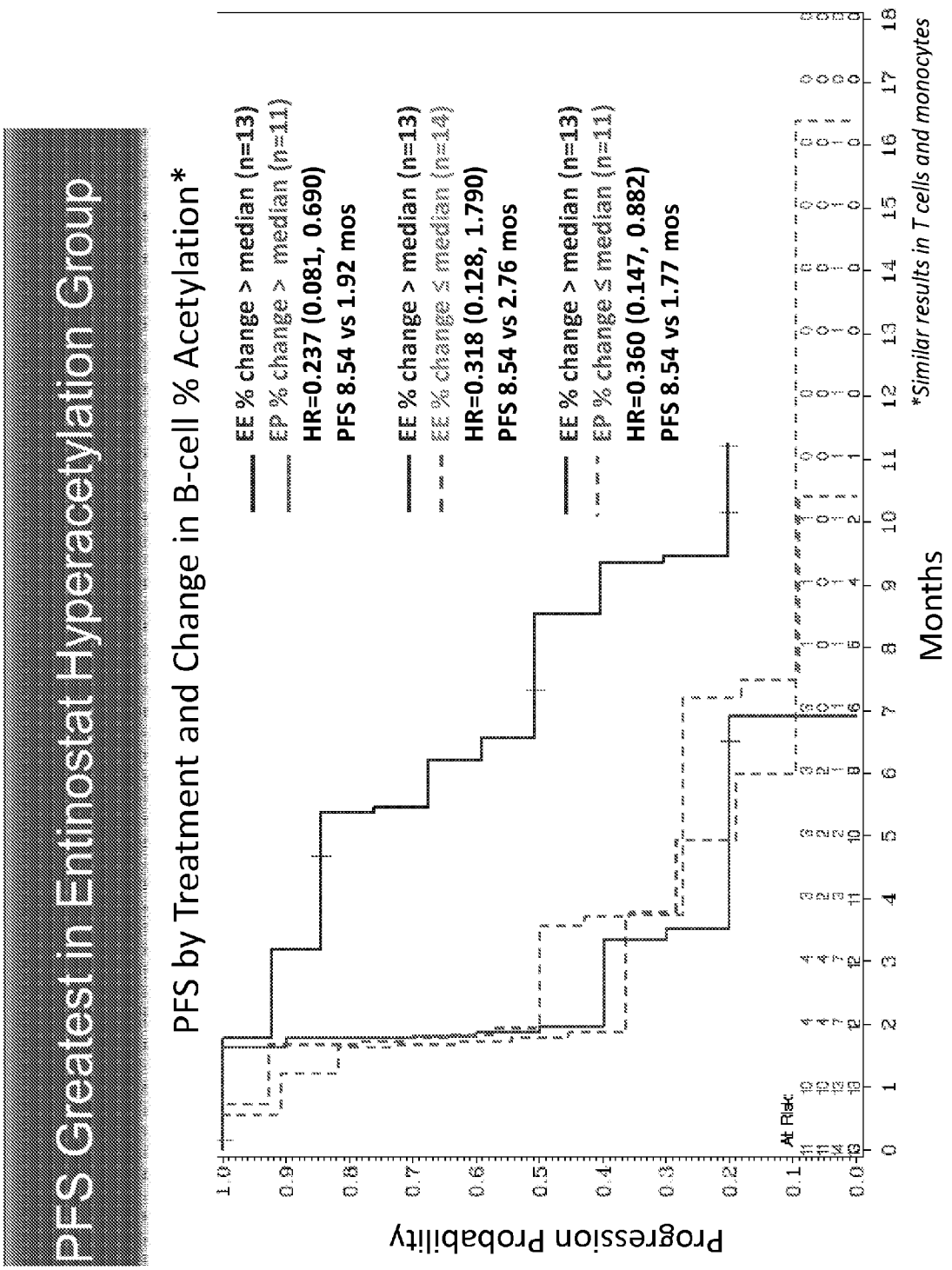
FIG. 29 provides a comparison of PFS to percent change of acetylation levels in each treatment arm in the Phase 2 study when the analysis is performed with B-cells.
Figure 30:
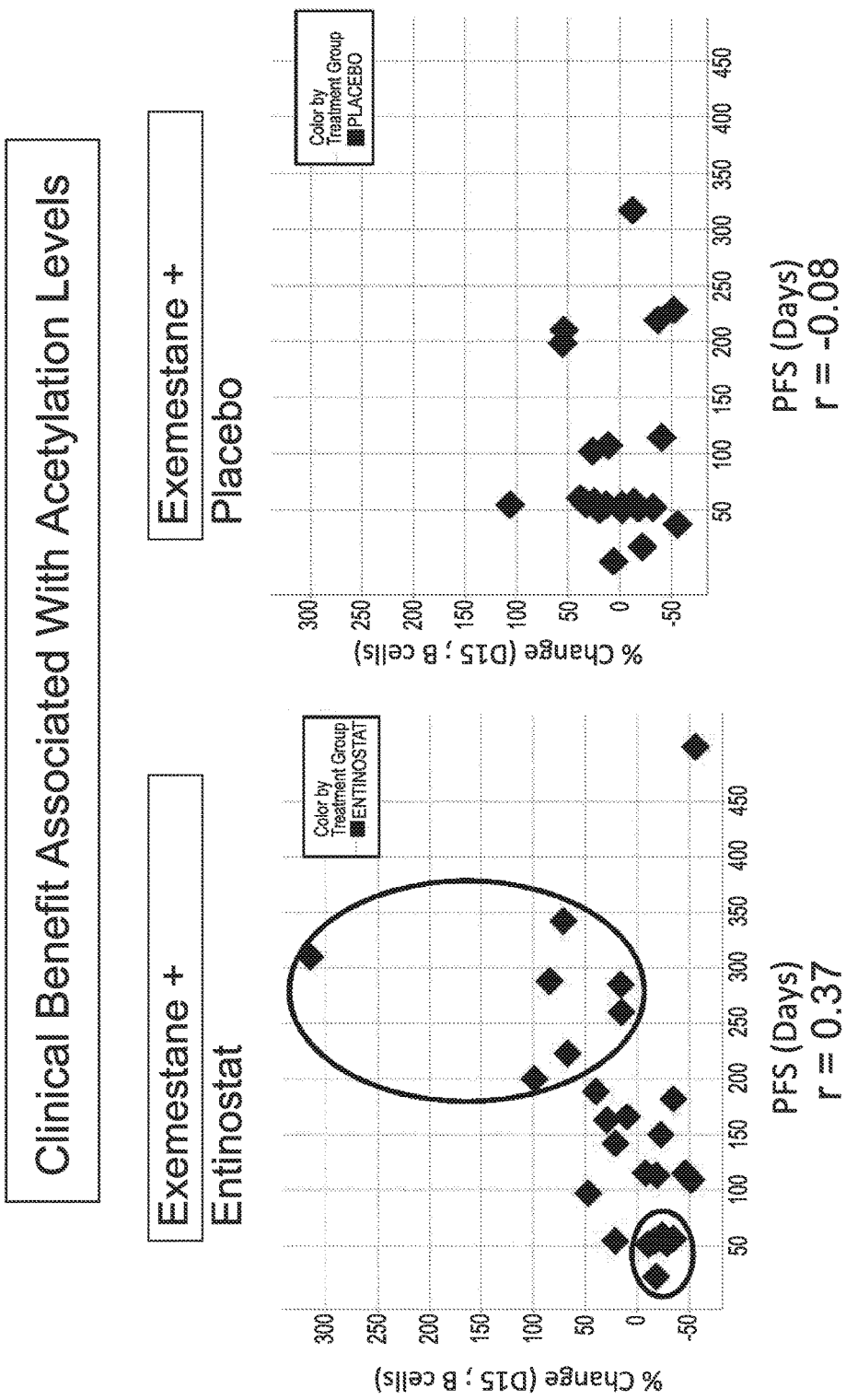
FIG. 30 illustrates that clinical benefit is associated with acetylation levels.
Figure 31:
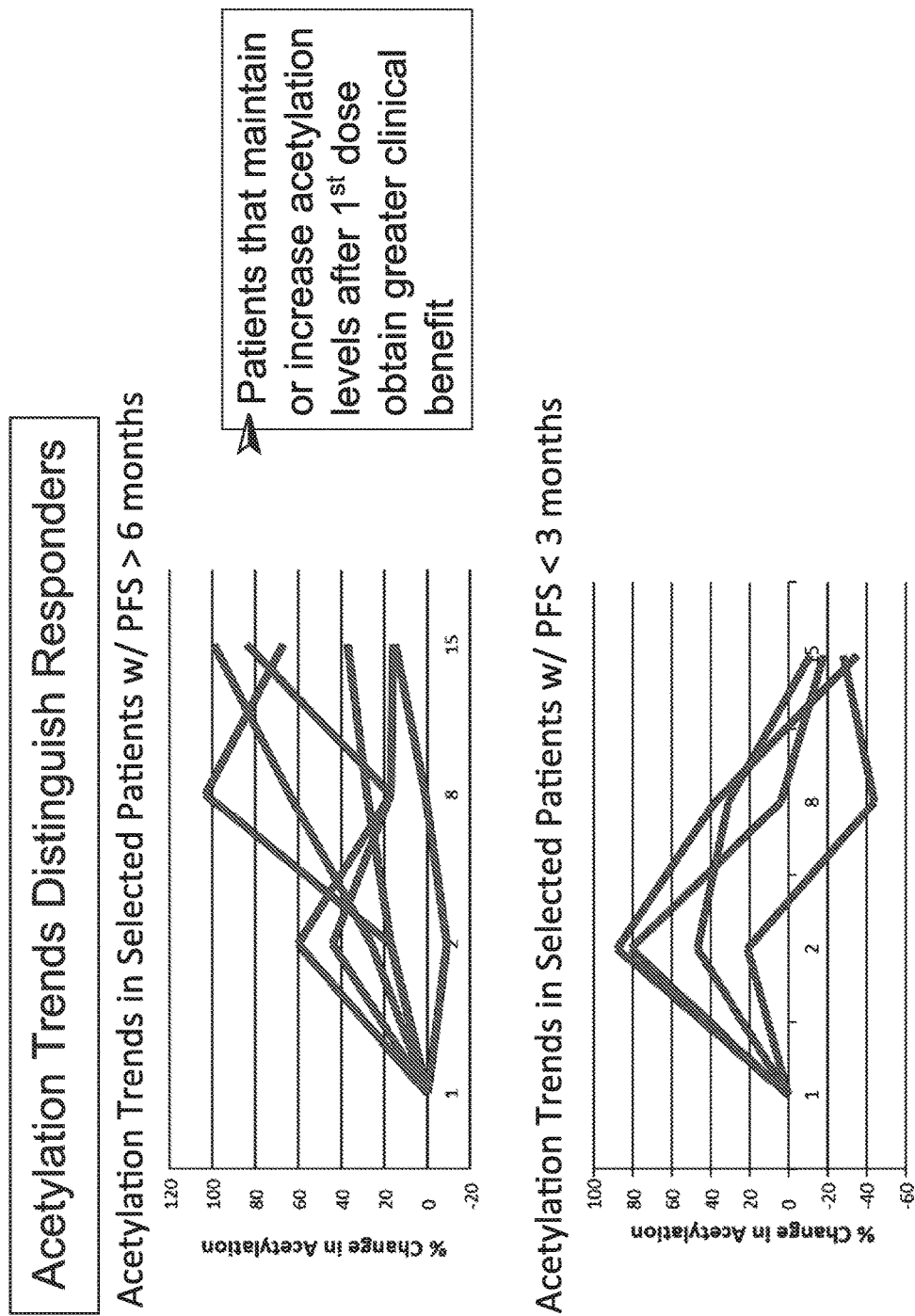
FIG. 31 illustrates that acetylation trends distinguish responders to treatment.
Figure 32:
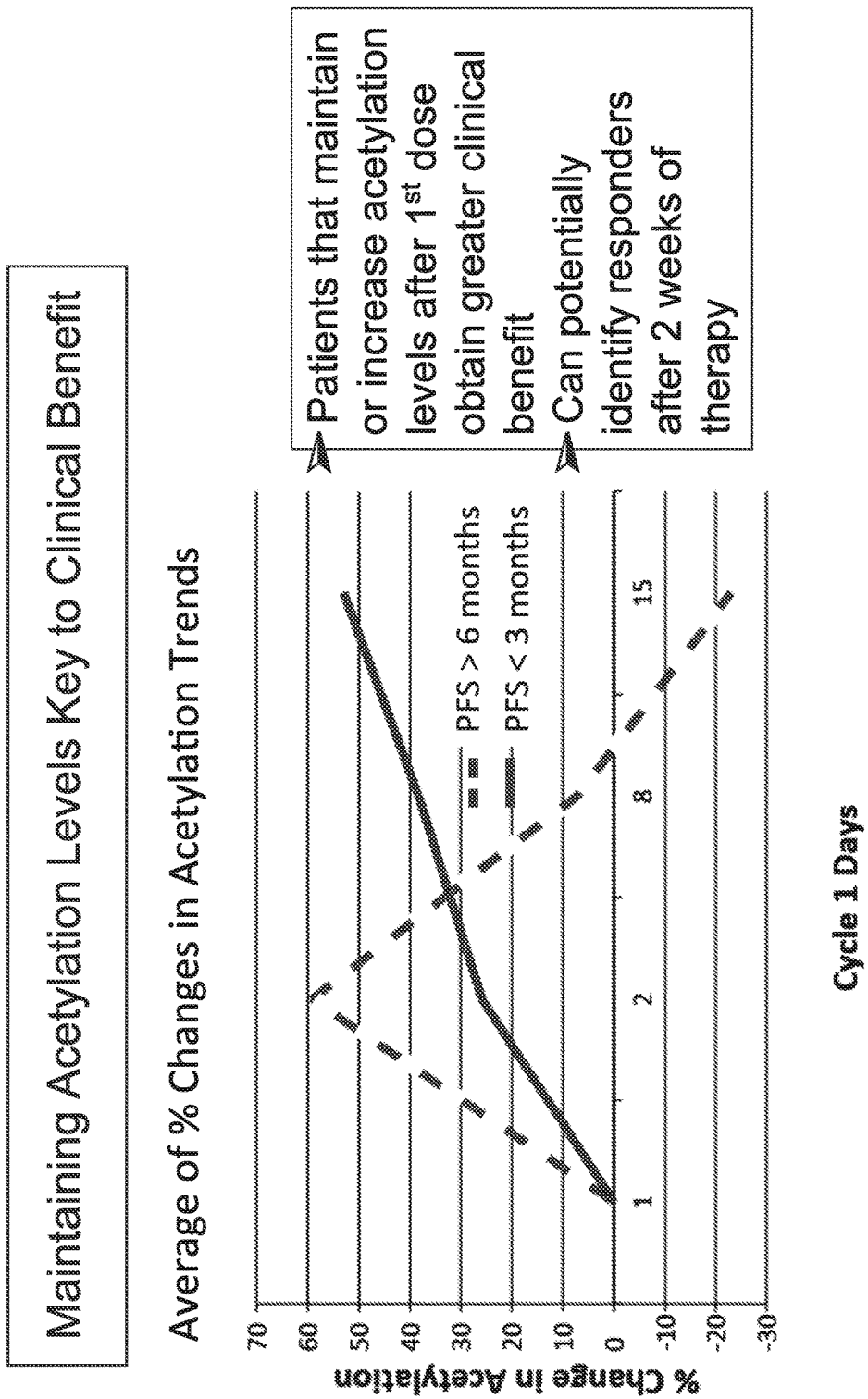
FIG. 32 illustrates that maintaining acetylation levels is key to obtaining a positive clinical outcome.

FIG. 25 provides a timeline for the dosing of entinostat and exemestane, and the timing of obtaining samples for acetylation analysis. FIG. 26 provides an analysis of change in acetylation levels versus PFS. FIG. 27 shows the average percent change in protein lysine acetylation from pre-treatment levels for monocyte, B-cell and T-cell tissue types. FIG. 28 provides Kaplan-Meier plots of PFS by treatment cohort for monocyte, B-cell and T-cell tissue types. PFS was found to be greatest for EE high acetylation patients. FIG. 29 provides a Kaplan-Meier plot of PFS by treatment cohort for the B-cell tissue samples and PFS was found to be greatest for EE high acetylation patients. FIG. 30 provides an analysis of PFS versus percent change for the EE and EP cohorts. FIG. 31 provides an analysis of acetylation trends over the course of treatment with respect to clinical outcome. Patients that maintain or increase acetylation levels after the first dose obtain greater clinical benefit. FIG. 32 illustrates that maintaining acetylation levels over the course of the treatment is a key to clinical benefit and it is possible to identify responders after two weeks of therapy. FIG. 33 provides a summary of the finding that protein lysine acetylation is linked to longer disease-free survival.

In conclusion, the addition of entinostat to exemestane prolonged PFS and OS in postmenopausal women with ER+ advanced BC that had progressed after treatment with a NSAI. A key finding of this study was the OS benefit observed in EE vs EP (28.1 versus 19.8 months; HR 0.59 [95% CI 0.36, 0.97] p=0.018). These results demonstrate for the first time that the addition of an epigenetic therapy (i.e., entinostat) to anti-estrogen therapy is an effective approach to targeting resistance pathways in BC, particularly in hormone-positive disease. Although entinostat added toxicity to the hormone therapy it was felt to have an acceptable safety profile for this patient population. More importantly and for the first time, an association of HDAC inhibition with entinostat-induced protein lysine acetylation and improved clinical outcomes was demonstrated in a subset of patients.

Example 2

Background:

Despite promising preclinical data and extensive clinical testing, histone deacetylase inhibitors (HDACi) as a class have not demonstrated significant activity in solid tumors as single agents or in combination. Even in indications (or settings) where HDACi have proven to be effective e.g. cutaneous or peripheral T-cell lymphomas, there is still an inability to identify those patients most likely to benefit because there has been no correlation found between outcome and acetylation.

Pharmacodynamic (PD) analysis of patient samples from ENCORE-301, a recently completed randomized phase 2 placebo-controlled study of exemestane with and without the HDACi entinostat in post-menopausal breast cancer patients (n=130), demonstrates an association of HDACi-induced lysine hyperacetylation with improved clinical outcome.

Methods:

Protein lysine acetylation is measured in circulating B cells (B), T cells (T) and monocytes (M) by multi-parameter flow cytometry from samples taken at pre-treatment, D1, D8, and D15 of cycle 1 from patients treated with exemestane plus entinostat (EE) or exemestane plus placebo (EP). Percent change is calculated and related to progression free survival (PFS) outcome data. Hyperacetylation independent of treatment arm is defined as a percent change increase above the calculated median percent change for each cell type.

Results:

Pre- and post treatment samples are obtained in a subset of 49 patients (EE=27; EP=22). Review of baseline characteristics in this subset indicates that they appear to be consistent with the entire population. Hyperacetylation across all cell types in EE vs EP is associated with prolonged median PFS (B: 8.54 months vs 1.92 HR=0.24 (95% CI 0.081, 0.690); T: 6.57 vs 1.77 HR=0.24 (95% CI 0.087, 0.640); M: 6.21 vs 1.87 HR=0.50 (95% CI 0.211, 1.203). Preliminary trends in overall survival also favor the EE hyperacetylation group. Samples taken for plasma concentration measurements of entinostat indicate that entinostat levels at the D8 and D15 time points used for the PD analysis are generally at or below the assay detection limits (<0.5 ng/ml) preventing a correlation to be made between acetylation increase and entinostat concentration. Characterization of adverse events with 10% or greater difference between treatments in the ENCORE-301 safety population (n=129) in the 49 patient biomarker patient subset indicates that thrombocytopenia incidence may be associated with hyperacetylation in the EE group while incidence of other AEs including fatigue do not appear to be associated with hyperacetylation.

Conclusion:

These data provide for the first time a clear association of HDACi-induced protein lysine hyperacetylation and clinical outcome. Several factors may contribute to the success in demonstrating this association including the randomized, controlled study design, positive outcome of ENCORE-301 and a sensitive pharmacodynamic assay that allows for measurement of global protein lysine acetylation changes. Combined with the overall positive results of ENCORE-301 (median PFS EE vs EP 4.28 vs 2.27 months HR 0.73 (95% CI 0.49, 1.09); and OS with median follow up of 18 months EE vs EP 26.9 vs 20.3 months HR 0.56 (95% CI 0.31, 1.02)), these data provide evidence of a potential breakthrough in the expansion of epigenetic therapy to solid tumors.

What is claimed is:

1. A method of treating breast cancer in a patient in need thereof, wherein the patient did not demonstrate a complete response, a partial response or stable disease for greater than six months during prior treatment with an aromatase inhibitor, the method comprising administering to the patient a combination therapy comprising entinostat and exemestane,
determining the level of protein lysine acetylation at about 15 days after initiating said combination therapy,
comparing the level of protein lysine acetylation prior to administration of the combination therapy, and
continuing the combination therapy if patient has an increase in the level of protein lysine acetylation prior to administration of the combination therapy, wherein the combination therapy comprises 5 mg of entinostat and 25 mg of exemestane.

2. The method of claim 1, wherein entinostat is administered weekly and the exemestane is administered daily.

3. The method of claim 1, wherein the patient relapsed during treatment on or within 6 months of completion of a prior non-steroidal aromatase inhibitor given as adjuvant therapy.

4. The method of claim 1, wherein the patient demonstrated progressive disease after at least 3 months treatment on prior non-steroidal aromatase inhibitor.

5. The method of claim 1, wherein the breast cancer is ER-positive.

6. The method of claim 1, wherein entinostat and exemestane are administered sequentially in either order or simultaneously.

7. The method of claim 1, wherein entinostat and exemestane are administered simultaneously.

8. The method of claim 1, wherein exemestane is administered first.

9. The method of claim 1, wherein exemestane is administered daily and the entinostat is administered periodically.

10. The method of claim 1, wherein entinostat is administered weekly and exemestane is administered daily.

11. The method of claim 1, wherein entinostat is introduced to an ongoing exemestane course of therapy.

12. The method of claim 1, wherein the increase is about 25%, about 50%, about 75%, about 100%, about 125%, or about 150%.

13. The method of claim 1, wherein the protein lysine acetylation levels are obtained from a tissue sample selected from B-cells, T-cells, or monocytes.

14. The method of claim 1, wherein the exemestane is administered daily.

15. The method of claim 1, wherein entinostat is administered every 7 days of a 28-day cycle.

16. The method of claim 1, wherein the combination therapy comprises oral administration of entinostat every 7 days of a 28-day cycle, and oral administration of exemestane every day.

17. The method of claim 1, wherein determining the protein lysine acetylation level during the course of therapy is performed more than once.

18. The method of claim 1, wherein determining the protein lysine acetylation level during the course of therapy is performed once.

* * * * *